US008318321B2

(12) United States Patent
Igawa et al.

(10) Patent No.: US 8,318,321 B2
(45) Date of Patent: Nov. 27, 2012

(54) COMPOUND AND ORGANIC LIGHT-EMITTING DEVICE

(75) Inventors: Satoshi Igawa, Fujisawa (JP); Shinjiro Okada, Kamakura (JP); Takao Takiguchi, Chofu (JP); Keiji Okinaka, Kawasaki (JP); Naoki Yamada, Inagi (JP); Masashi Hashimoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 501 days.

(21) Appl. No.: 11/913,054

(22) PCT Filed: Dec. 8, 2006

(86) PCT No.: PCT/JP2006/324997
§ 371 (c)(1),
(2), (4) Date: Oct. 29, 2007

(87) PCT Pub. No.: WO2007/072742
PCT Pub. Date: Jun. 28, 2007

(65) Prior Publication Data
US 2009/0079331 A1   Mar. 26, 2009

(30) Foreign Application Priority Data

Dec. 20, 2005   (JP) ................................. 2005-366559
May 15, 2006    (JP) ................................. 2006-135070
Oct. 12, 2006   (JP) ................................. 2006-278926

(51) Int. Cl.
*H01L 51/54*   (2006.01)
(52) U.S. Cl. ........ 428/690; 428/917; 313/504; 313/505; 313/506; 257/40; 257/E51.05; 257/E51.026; 257/E51.032; 585/267
(58) Field of Classification Search .......... 428/690, 428/917; 257/40, E51.05, E51.026, E51.032; 313/504, 505, 506; 585/27
See application file for complete search history.

(56) References Cited

U.S. PATENT DOCUMENTS

| 7,241,513 B2 | 7/2007 | Suzuki et al. ................. 428/690 |
| 2003/0087126 A1 | 5/2003 | Ishida et al. ................. 428/690 |
| 2004/0253389 A1* | 12/2004 | Suzuki et al. ................. 428/1.1 |
| 2005/0236977 A1 | 10/2005 | Yamada et al. ............... 313/504 |
| 2006/0121312 A1* | 6/2006 | Yamada et al. ............... 428/690 |
| 2006/0159956 A1 | 7/2006 | Ito et al. ........................ 428/690 |
| 2007/0111029 A1 | 5/2007 | Yamada et al. ............... 428/690 |

FOREIGN PATENT DOCUMENTS

| JP | 2003-229273 | 8/2003 |
| JP | 2003-313546 | 11/2003 |
| JP | 2004-043349 | 2/2004 |
| JP | 2004-83481 | 3/2004 |
| WO | 2004020372 A1 | 3/2004 |
| WO | WO 2005/090365 A1 | 9/2005 |

OTHER PUBLICATIONS

Database CA Chemical Abstracts Services, (Oct. 7, 2005), of article of Chen, Andrew C.—A. et al: Novel light-emitting organic materials with variable electron and hole conductivities XP002596386—1 page.
Supplementary European Search Report issued in the counterpart application No. 06842828.3 dated Sep. 1, 2010—7 pages.
European Communication issued in the counterpart application No. 06842828.3 dated Jun. 28, 2012—6 pages.

* cited by examiner

*Primary Examiner* — Jennifer Chriss
*Assistant Examiner* — Gregory Clark
(74) *Attorney, Agent, or Firm* — Fitzpatrick, Cella, Harper & Scinto

(57) ABSTRACT

There are provided a compound represented by the general formula (1) and an organic light-emitting device which comprises the compound and has an optical output with remarkably high efficiency and high luminance.

10 Claims, 3 Drawing Sheets

COMPOUND AND ORGANIC LIGHT-EMITTING DEVICE

TECHNICAL FIELD

The present invention relates to a light-emitting device using an organic compound, and more particularly to a compound of a specific molecular structure and an organic EL device using the compound.

BACKGROUND ART

An organic light-emitting device has a structure in which a thin film comprising a fluorescent organic compound or phosphorescent organic compound is interposed between an anode and a cathode. By injecting electrons and holes (positive holes) from the electrodes into the device, excitons of the fluorescent organic compound or phosphorescent organic compound are generated, and light radiated when the excitons return to a ground state is utilized.

Further, the recent progress of the organic light-emitting device is remarkable, and is characterized in that a highly responsive, thin, and lightweight light-emitting device that can be driven at a low applied voltage and provides a high luminance and a variety of emission wavelengths can be made, which suggests the applicability to a wide variety of uses.

However, at present, an optical output of a higher luminance or light emission of a higher conversion efficiency is still required. Further, there still remain a large number of problems in terms of durability such as a time-dependent change due to long-term use and deterioration due to an atmospheric gas containing oxygen or to moisture. Moreover, when application to a full-color display or the like is attempted, emission of blue, green and red lights with high color purities is necessary, but these problems have not satisfactorily been solved yet.

As patent documents which disclose compounds comprising fluorene and fused rings, there are included Japanese Patent Application Laid-Open Nos. 2003-229273 and 2004-43349, but the patent publications have no specific description about the organic compound of an asymmetric molecular structure with a molecular structural formula comprising oligofluorene and a fused polycyclic aromatic group with four or more rings according to the present invention.

DISCLOSURE OF THE INVENTION

It is, therefore, an object of the present invention to provide a novel compound of an asymmetric molecular structure comprising oligofluorene and a substituted or unsubstituted fused polycyclic aromatic group with four or more rings.

It is another object of the present invention to provide an organic light-emitting device which uses the above-mentioned compound and has an optical output with remarkably high efficiency and high luminance.

It is still another object of the present invention to provide an organic light-emitting device which exhibits remarkably good durability.

It is yet another object of the present invention to provide an organic light-emitting device which can easily be produced at a relatively low cost.

That is, the present invention provides the followings:

(1) A compound represented by the following general formula (I):

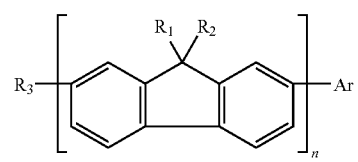

(I)

wherein $R_1$ and $R_2$ each represent, independently of one another, a hydrogen atom, a substituted or unsubstituted alkyl group, a substituted or unsubstituted aralkyl group, a substituted or unsubstituted aryl group, or a substituted or unsubstituted heterocyclic group;

$R_3$ represents a hydrogen atom, a linear, branched, or cyclic alkyl group (at least one methylene group of the alkyl group may be replaced by —O—, —S—, —CO—, —CO—O—, —O—CO—, —CH=CH—, —C≡C—, a substituted or unsubstituted arylene group, or a substituted or unsubstituted heterocyclic group, and a hydrogen atom of the alkyl group may be replaced by a fluorine atom), a substituted or unsubstituted aryl group with one or two rings (at least one CH of the aryl group may be replaced by a nitrogen atom);

Ar represents a substituted or unsubstituted fused polycyclic aromatic group with four or more rings;

n represents an integer of 2 to 10; and the plurality of fluorene-2,7-diyl groups may each independently have a substituent and may be the same or different from each other.

(2) A compound set forth in (1) above in which Ar of the general formula (I) is a fused polycyclic aromatic group represented by the following general formula (II):

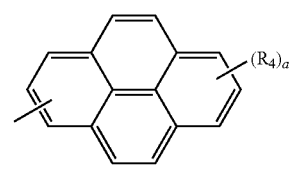

(II)

wherein $R_4$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, or a halogen atom;

a represents an integer of 1 to 9; and when $R_4$ is present in plurality, $R_4$'s may be the same or different from each other.

(3) A compound set forth in (1) above and represented by the following general formula (III):

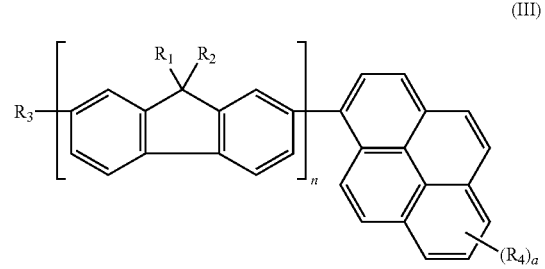

(III)

wherein $R_1$ and $R_2$ each represent, independently of one another, a hydrogen atom, a substituted or unsubstituted alkyl group, a substituted or unsubstituted aralkyl group, a substituted or unsubstituted aryl group, or a substituted or unsubstituted heterocyclic group;

$R_3$ represents a hydrogen atom, a linear, branched, or cyclic alkyl group (at least one methylene group of the alkyl group may be replaced by —O—, —S—, —CO—, —CO—O—, —O—CO—, —CH=CH—, —C≡C—, a substituted or unsubstituted arylene group, or a substituted or unsubstituted heterocyclic group, and a hydrogen atom of the alkyl group may be replaced by a fluorine atom), a substituted or unsubstituted aryl group with one or two rings (at least one CH of the aryl group may be replaced by a nitrogen atom);

$R_4$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, or a halogen atom;

a represents an integer of 1 to 9;

when $R_4$ is present in plurality, $R_4$'s may be the same or different from each other;

n represents an integer of 2 to 10; and the plurality of fluorene-2,7-diyl groups may each independently have a substituent and may be the same or different from each other.

(4) A compound set forth in (1) above in which Ar of the general formula (I) is a fused polycyclic aromatic group represented by the following general formula (IV):

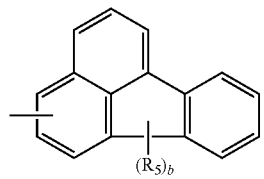

(IV)

wherein $R_5$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, or a halogen atom;

b represents an integer of 1 to 9; and when $R_5$ is present in plurality, $R_5$'s may be the same or different from each other.

(5) A compound set forth in (1) above and represented by the following general formula (V)

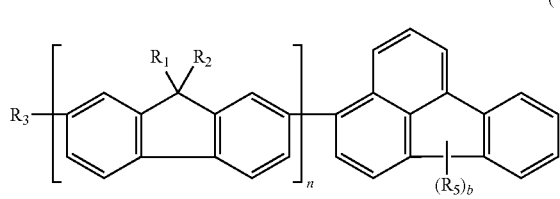

(V)

wherein $R_1$ and $R_2$ each represent, independently of one another, a hydrogen atom, a substituted or unsubstituted alkyl group, a substituted or unsubstituted aralkyl group, a substituted or unsubstituted aryl group, or a substituted or unsubstituted heterocyclic group;

$R_3$ represents a hydrogen atom, a linear, branched, or cyclic alkyl group (at least one methylene group of the alkyl group may be replaced by —O—, —S—, —CO—, —CO—O—, —O—CO—, —CH=CH—, —C≡C—, a substituted or unsubstituted arylene group, or a substituted or unsubstituted heterocyclic group, and a hydrogen atom of the alkyl group may be replaced by a fluorine atom), a substituted or unsubstituted aryl group with one or two rings (at least one CH of the aryl group may be replaced by a nitrogen atom);

$R_5$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, or a halogen atom;

b represents an integer of 1 to 9;

when $R_5$ is present in plurality, $R_5$'s may be the same or different from each other;

n represents an integer of 2 to 10; and the plurality of fluorene-2,7-diyl groups may each independently have a substituent and may be the same or different from each other.

(6) A compound set forth in (1) above in which n of the general formula (I) is an integer of 2 to 4.

(7) An organic light-emitting device which comprises a pair of electrodes including an anode and a cathode, and a layer comprising an organic compound provided between the pair of electrodes, wherein the layer comprising the organic compound comprises at least one of the compounds set forth in (1).

(8) An organic light-emitting device set forth in (7) above in which the layer is a light-emitting layer.

(9) An organic light-emitting device set forth in (7) above in which the layer comprising the organic compound is a light-emitting layer which comprises at least two compounds of a host and a guest.

(10) An organic light-emitting device set forth in (7) above which is an electroluminescent device that emits light by application of a voltage to the pair of electrodes.

The compound of the present invention has a high glass transition temperature, and the light-emitting device using the compound as a host or guest of a light-emitting layer according to the present invention provides a high-efficiency light emission, maintains a high luminance for a period of time longer than those of the commonly used compounds, and is therefore an excellent device.

More specifically, the compound represented by the general formula (I) has a high glass transition temperature and is excellent in stability when formed in a thin film.

Further, the organic light-emitting device using the compound as a host or guest of a light-emitting layer provides light emission with a high luminance at a low applied voltage and is also excellent in durability.

Moreover, the device can be produced by use of a vacuum vapor deposition or casting method, and a relatively low-cost, large-area device can easily be produced.

BEST MODE FOR CARRYING OUT THE INVENTION

Figure 1:
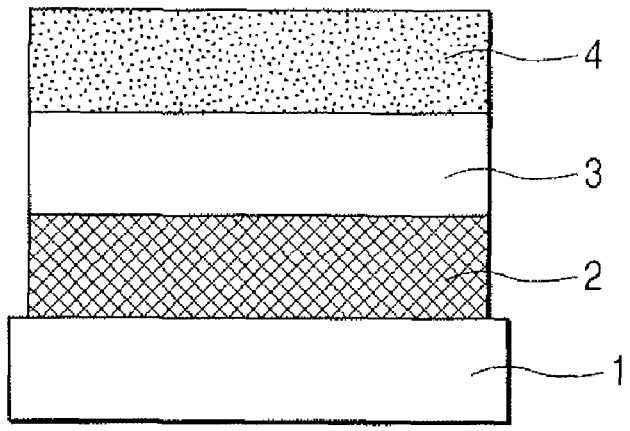
FIG. 1 is a schematic cross-sectional view showing an example of the organic light-emitting device in accordance with the present invention.

The present invention will now be described in detail.

First, there are shown below specific examples of the substituents in the general formulae (I), (III), and (V), which are, however, given for the purpose of illustration and not by way of limitation.

As the alkyl group, there are included methyl group, ethyl group, normal propyl group, isopropyl group, normal butyl group, tertiary butyl group, hexyl group, octyl group, cyclohexyl group, trifluoromethyl group, and the like.

As the aralkyl group, there are included benzyl group, phenethyl group, and the like.

As the aryl group, there are included phenyl group, biphenyl group, terphenyl group, and the like.

As the heterocyclic group, there are included thienyl group, pyrrolyl group, pyridyl group, oxazolyl group, oxadiazolyl group, thiazolyl group, thiadiazolyl group, terthienyl group, and the like.

As the substituted amino group, there are included dimethylamino group, diethylamino group, dibenzylamino group, diphenylamino group, ditolylamino group, dianisolylamino group, and the like.

As the halogen atom, there are included fluorine, chlorine, bromine, iodine, and the like.

As the fused polycyclic aromatic group, there are included fluorenyl group, naphthyl group, fluoranthenyl group, anthryl group, phenanthryl group, pyrenyl group, tetracenyl group, pentacenyl group, triphenylenyl group, perylenyl group, and the like.

As the fused polycyclic aromatic group with four or more rings, there are included pyrenyl group, fluoranthenyl group, benzofluoranthenyl group, tetracenyl group, pentacenyl group, triphenylenyl group, perylenyl group, chrysenyl group, and the like.

As the aryl group with one or two rings, there are included phenyl group, naphthyl group, pyridyl group, quinolyl group, isoquinolyl group, biphenyl group, and the like.

As the substituents which the above described substituents may further posses, there are included alkyl groups such as methyl group, ethyl group, and propyl group; aralkyl groups such benzyl group and phenethyl group; aryl groups such as phenyl group and biphenyl group; heterocyclic groups such as thienyl group, pyrrolyl group, and pyridyl group; amino groups such as dimethylamino group, diethylamino group, dibenzylamino group, diphenylamino group, ditolylamino group, and dianisolylamino group; alkoxyl groups such as methoxyl group, ethoxyl group, propoxyl group, and phenoxyl group; and halogen atoms such as fluorine, chlorine, bromine, and iodine.

When a light-emitting layer comprises a carrier transporting host material and a guest, the process for light emission is composed of the following several steps.

1. Transportation of electrons/holes in the light-emitting layer
2. Generation of excitons in the host
3. Transmission of excitation energy between host molecules
4. Transfer of the excitation energy from the host to the guest The desired energy transfer and light emission in the respective steps are caused in competition with various deactivation steps.

It is needless to say that in order to increase the emission efficiency of an EL device, the emission quantum yield of a luminescent center material itself must be large. However, how high efficiency of energy transfer between hosts or between a host and a guest can be achieved is also a large problem. In addition, the cause for deterioration of light emission due to energization has not been clarified yet. However, it is assumed that the deterioration is related at least to a luminescent center material itself or an environmental change of a light-emitting material due to surrounding molecules.

In view of the above, the present inventors have made various studies to find that a device using the compound represented by the general formula (I) as a host or guest of a light-emitting layer emits light with a high efficiency, maintains a high luminance for a long period of time, and shows less deterioration due to energization.

One possible cause for the deterioration of light emission due to energization is deterioration of light emission due to deterioration of a thin-film shape of a light-emitting layer. It is believed that the deterioration of the thin-film shape results from crystallization of an organic thin film due to the temperature of drive environment or heat generation at the time of driving a device. This is considered to originate from a low glass transition temperature of a material, so that an organic EL material is required to have a high glass transition temperature. The compound represented by the general formula (I) of the present invention has a high glass transition temperature, so that the durability of an organic EL device is expected to increase.

The compound of the present invention will be described in more detail.

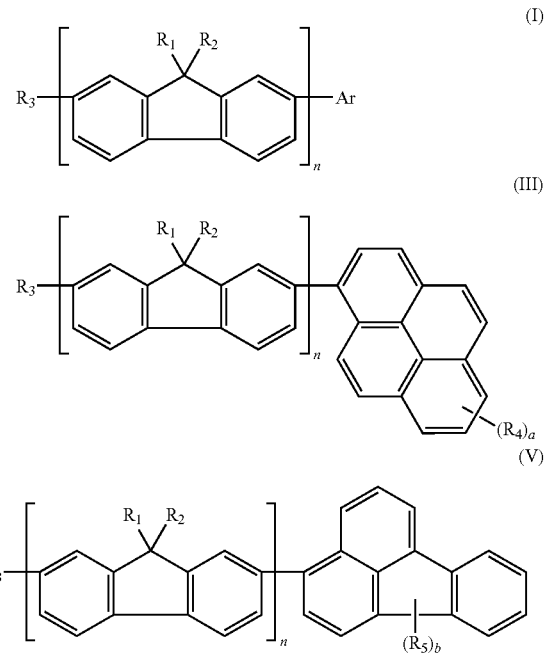

In the above formulae, $R_1$ and $R_2$ are each selected from a hydrogen atom; a substituted or unsubstituted alkyl group such as methyl group, ethyl group, normal propyl group, isopropyl group, normal butyl group, tertiary butyl group, hexyl group, octyl group, cyclohexyl group, or trifluoromethyl group; a substituted or unsubstituted aralkyl group such as benzyl group; a substituted or unsubstituted aryl group such as phenyl group or naphthyl group; and a substituted or unsubstituted heterocyclic group such as pyridyl group. In consideration of the stability of the position 9 carbon atom of the fluorenediyl group against radicals, the alkyl group is preferable. Further, since it is considered that when the alkyl chain at the position 9 of the fluorenediyl group is long, the glass transition temperature will be decreased, it is preferred to select an alkyl group with a short carbon chain such as methyl group, ethyl group, or the like. Moreover, although $R_1$ and $R_2$ may be the same or different from each other, it is preferred from the viewpoint of easiness of synthesis that $R_1$ and $R_2$ are be the same.

$R_3$ is selected from a hydrogen atom; an alkyl group such as methyl group, ethyl group, normal propyl group, isopropyl group, normal butyl group, tertiary butyl group, octyl group, cyclohexyl group, or trifluoromethyl group; a substituted or unsubstituted aryl group with one or two rings such as phenyl group, naphthyl group, pyridyl group, quinolyl group, or isoquinolyl group.

It is considered that when a substituted or unsubstituted fused polycyclic aromatic group with three or less rings is used for Ar, the bandgap of the molecule becomes broader to cause emission of ultraviolet light and the charge transporting property is lowered, so that even when used as a host, the drive voltage of the device becomes high. As the fused polycyclic aromatic group with four or more rings, there are included pyrenyl group, fluoranthenyl group, benzofluoranthenyl group, tetracenyl group, pentacenyl group, triphenylenyl group, perylenyl group, chrysenyl group, and the like. When considering the use for a blue-light-emitting material or a host material, it is preferable to select pyrenyl group, fluoranthenyl group, or benzofluoranthenyl group.

$R_4$ and $R_5$ are each selected from a hydrogen atom; a substituted or unsubstituted alkyl group such as methyl group, ethyl group, normal propyl group, isopropyl group, normal butyl group, tertiary butyl group, hexyl group, octyl group, cyclohexyl group, or trifluoromethyl group; a substituted or unsubstituted aralkyl group such as benzyl group; a substituted or unsubstituted aryl group such as phenyl group or naphthyl group; a substituted or unsubstituted heterocyclic group such as pyridyl group; a substituted amino group such as dimethylamino group or diphenylamino group; and a halogen atom such as fluorine.

n represents an integer of 2 to 10 with 2 to 4 being preferred from the viewpoint of vapor deposition property and easiness of synthesis. It is considered that when n is 1, the molecular weight of the compound is small, whereby the glass transition temperature becomes low. Further, the compound of the present invention has an asymmetric molecular structure and is less susceptible to crystallization and the like even at temperatures above the glass transition temperature, thus being excellent in stability over time.

In addition, it is generally known that a fused polycyclic aromatic compound with a large size is susceptible to intermolecular stacking or formation of molecular aggregates. It is considered that because of having the asymmetric molecular structure, the compound of the present invention can suppress stacking of a fused polycyclic aromatic group with four or more rings.

Moreover, the plurality of fluorene-2,7-diyl groups may be the same or different from each other and may each independently have a substituent.

Next, specific structural formulae of organic compounds used in the present invention will be given below. However, it should be understood that the same is by way of illustration and example only and the invention is not limited thereto.

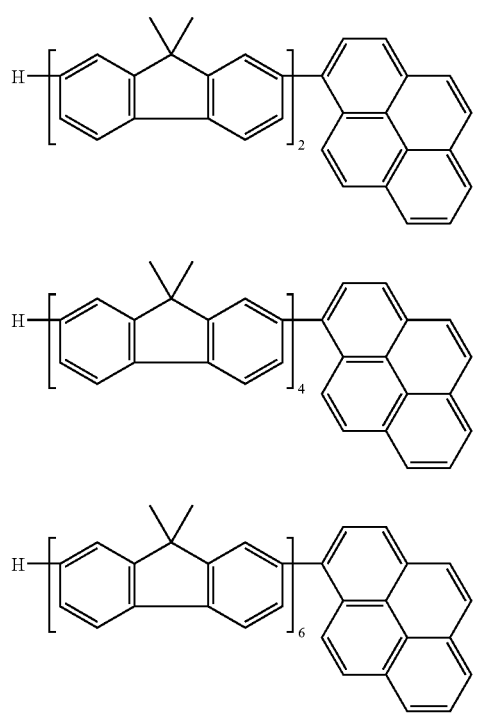
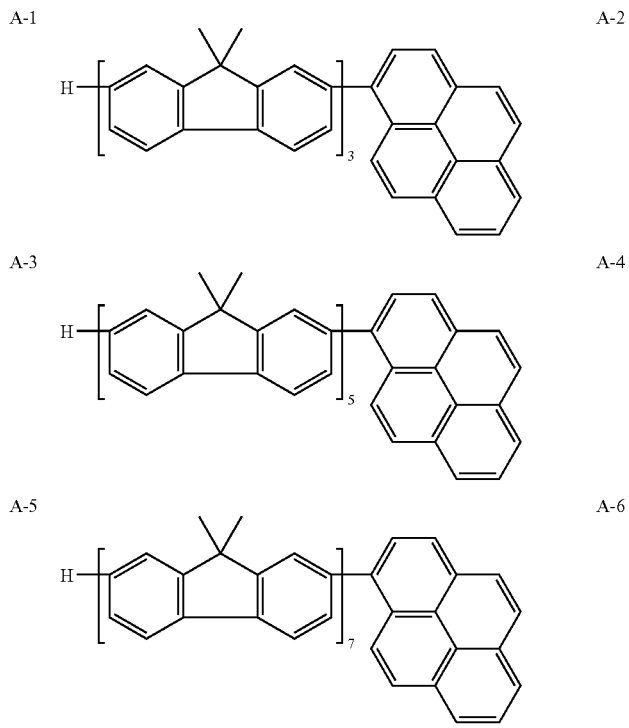

-continued
A-7
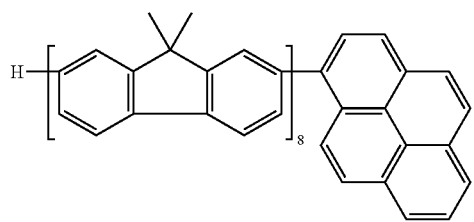
A-8
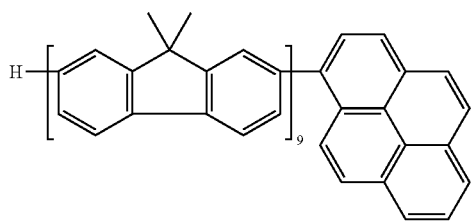
A-9
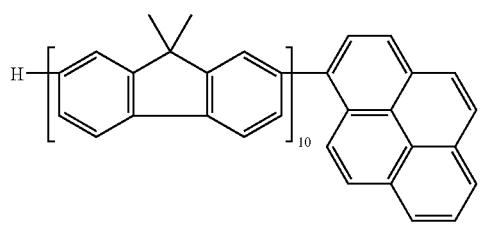
A-10
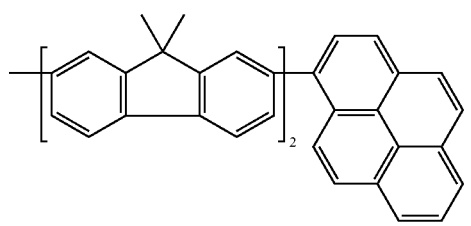
A-11
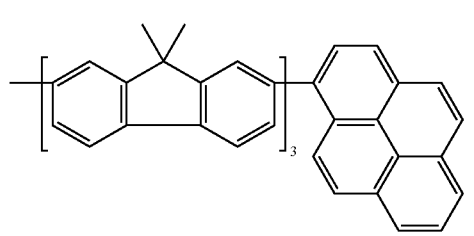
A-12
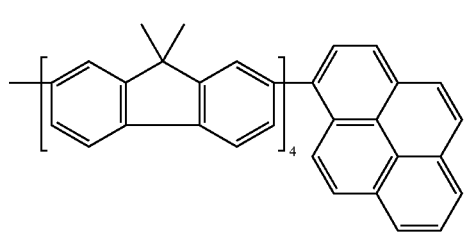
A-13
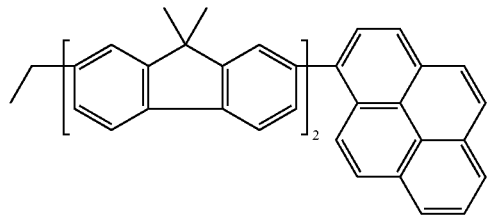
A-14
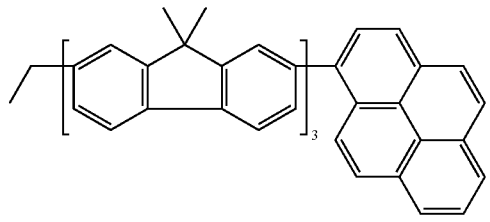
A-15
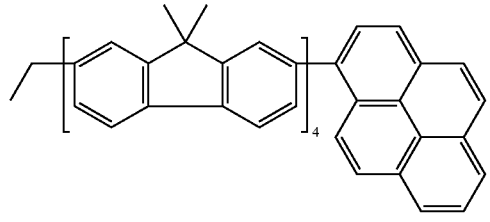
A-16
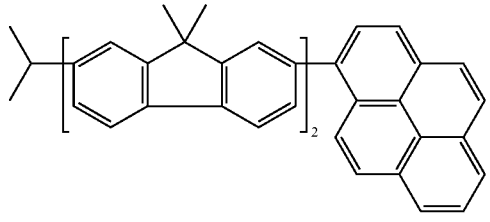
A-17
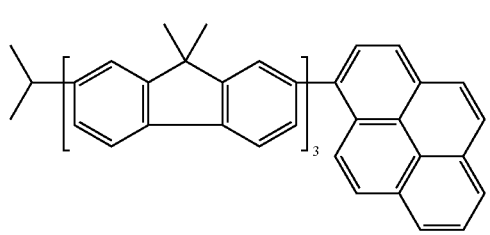
A-18
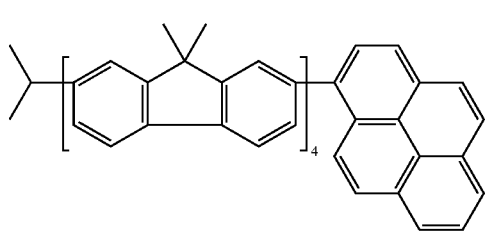
A-19
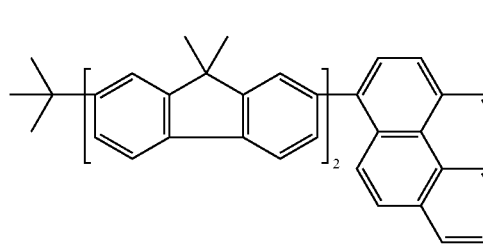
A-20
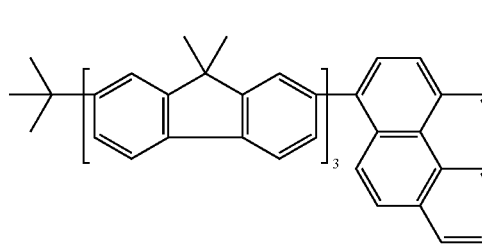

-continued
A-21
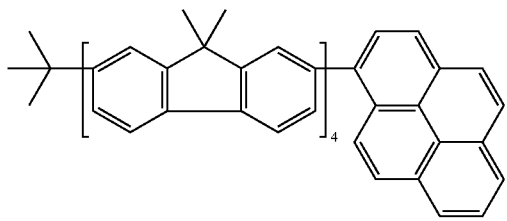
A-22
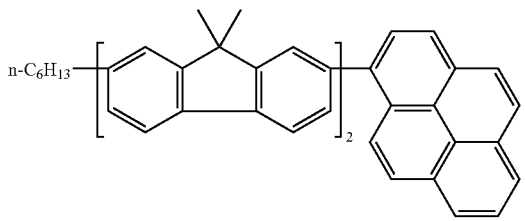
A-23
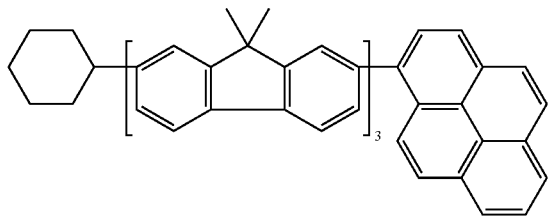
A-24
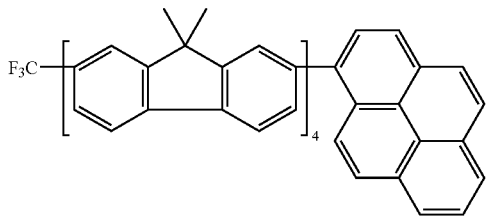
A-25
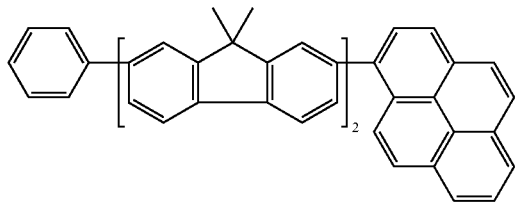
A-26
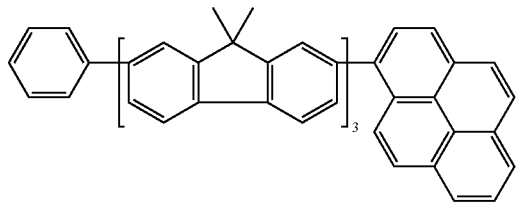
A-27
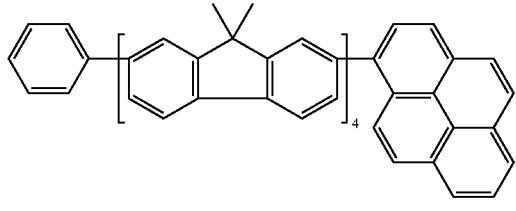
A-28
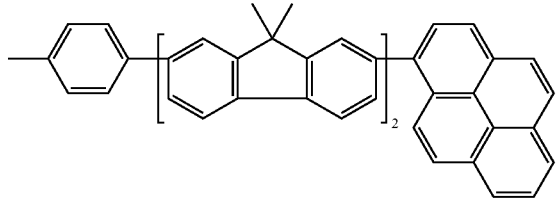
A-29
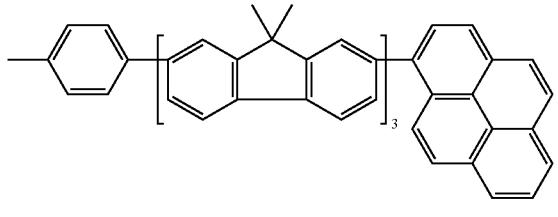
A-30
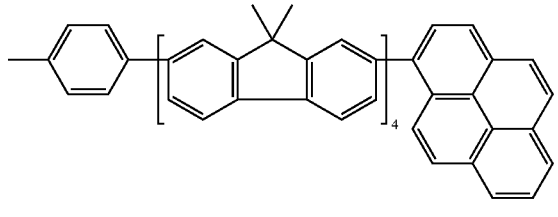
A-31
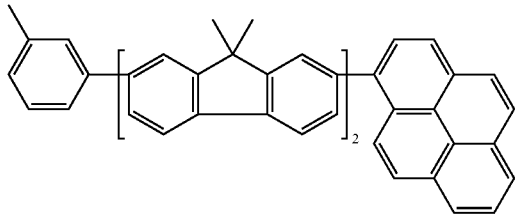
A-32
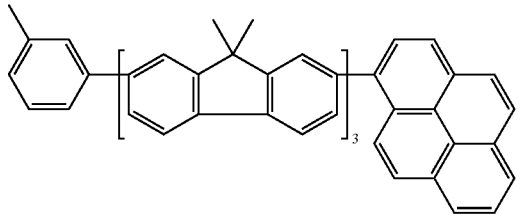

-continued
A-33
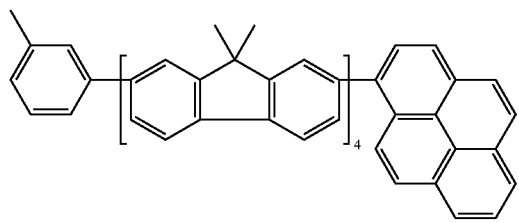
A-34
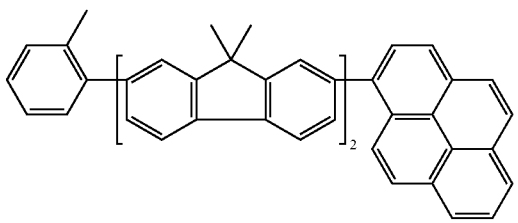
A-35
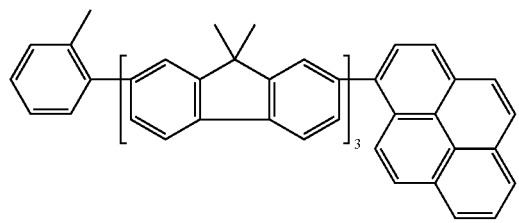
A-36
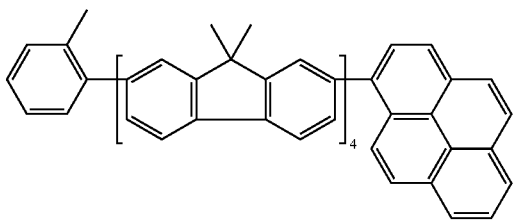
A-37
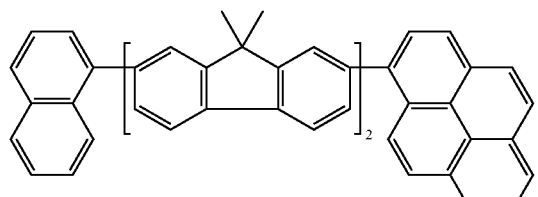
A-38
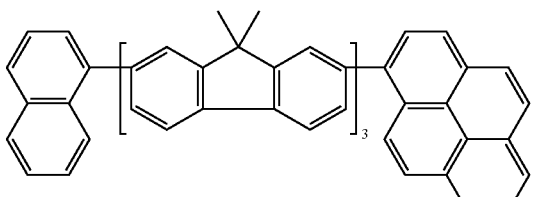
A-39
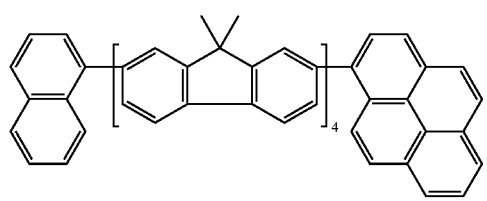
A-40
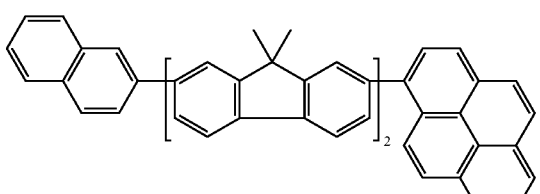
A-41
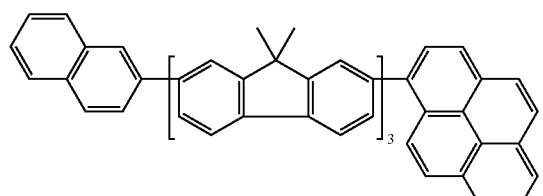
A-42
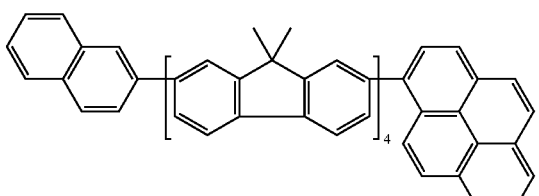
A-43
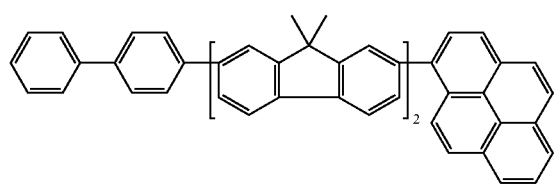
A-44
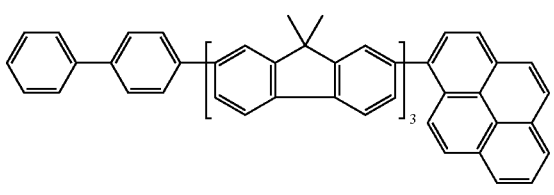
A-45
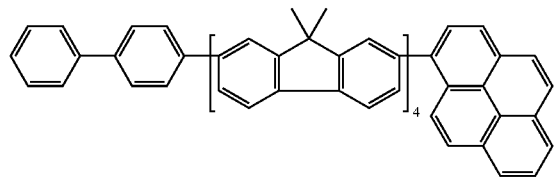
A-46
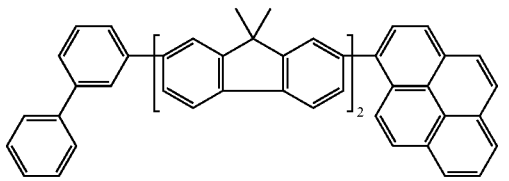

-continued
A-47
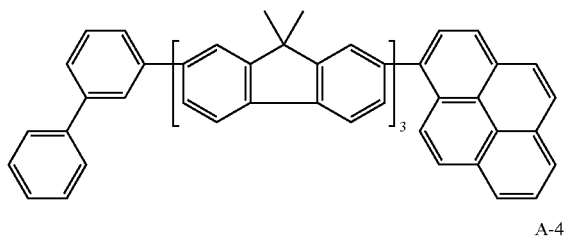
A-48
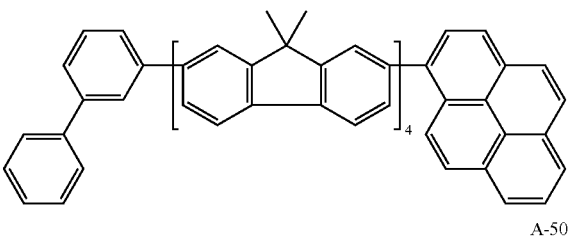
A-49
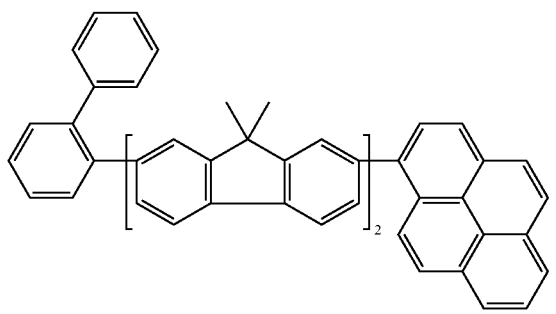
A-50
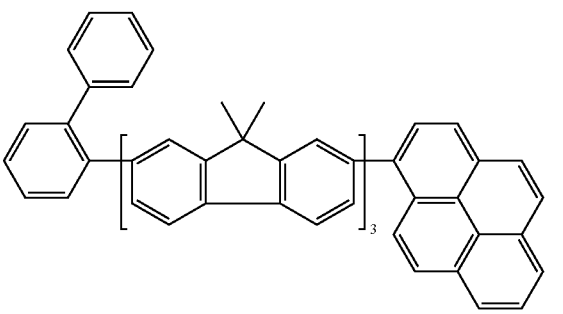
A-51
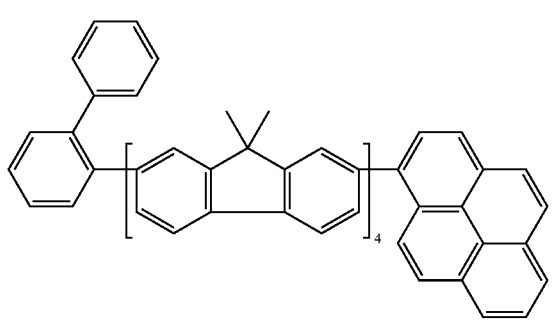
A-52
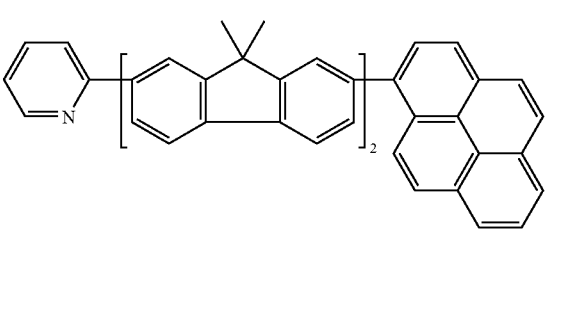
A-53
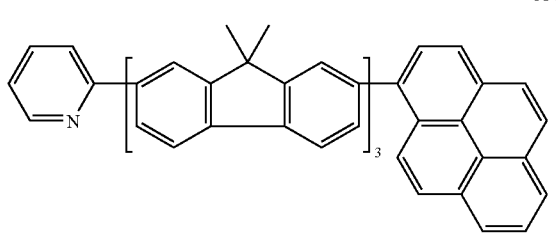
A-54
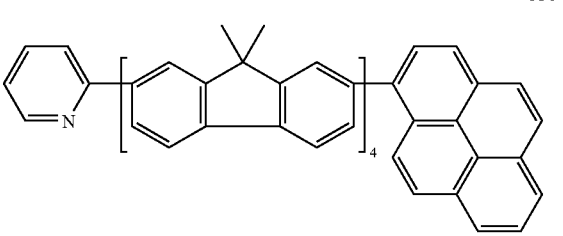
A-55
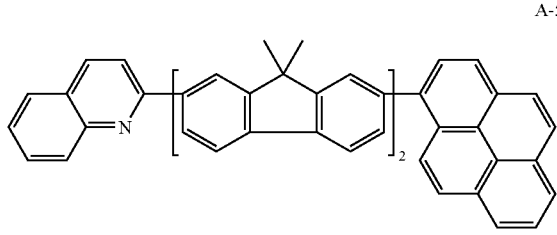
A-56
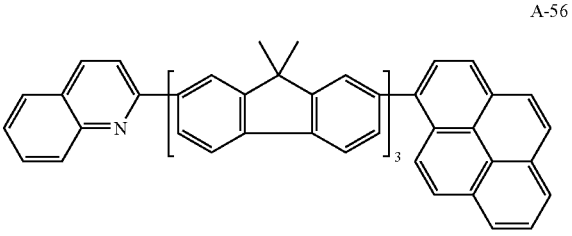
A-57
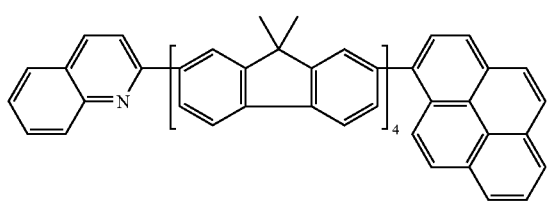
A-58
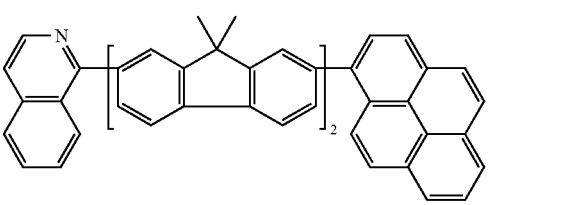

-continued
A-59
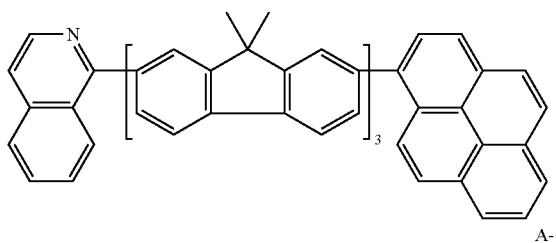
A-60
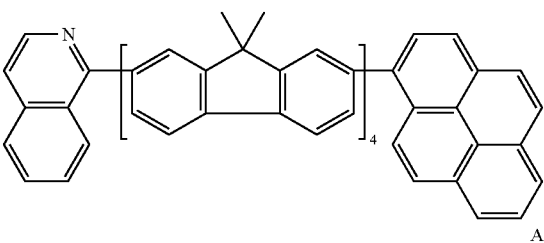
A-61
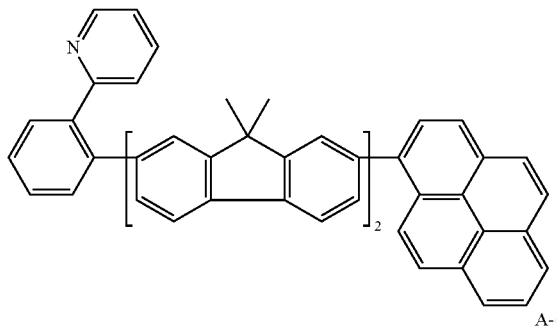
A-62
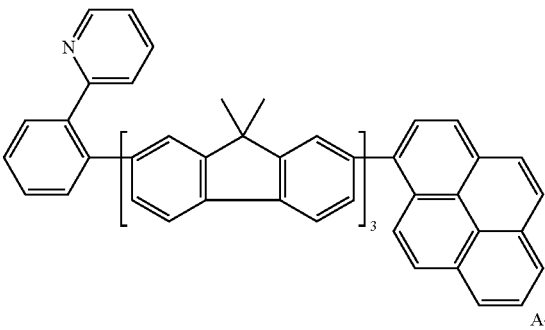
A-63
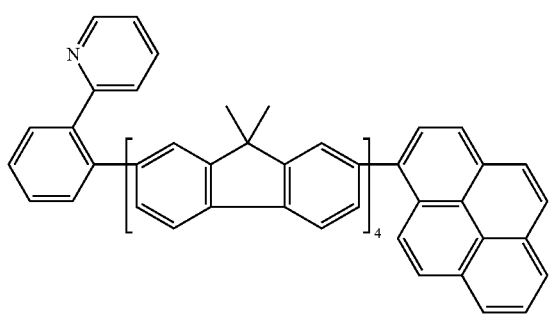
A-64
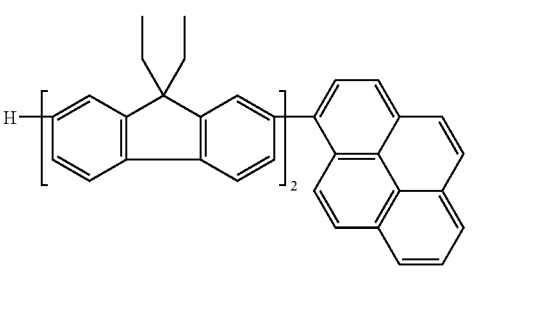
A-65
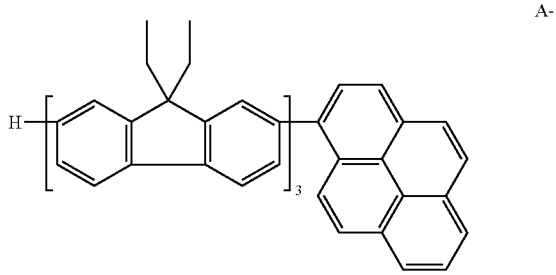
A-66
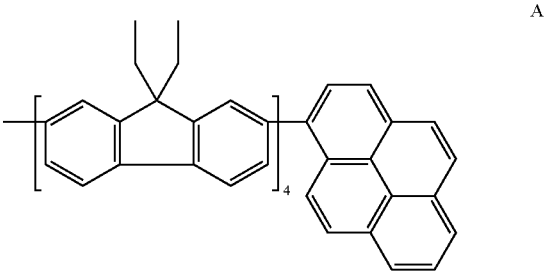
A-67
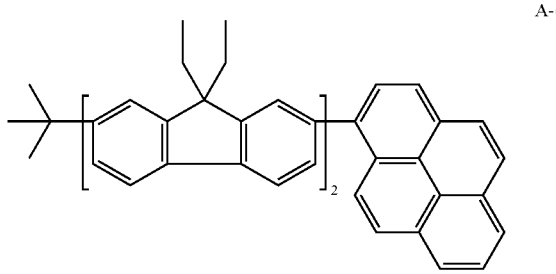
A-68
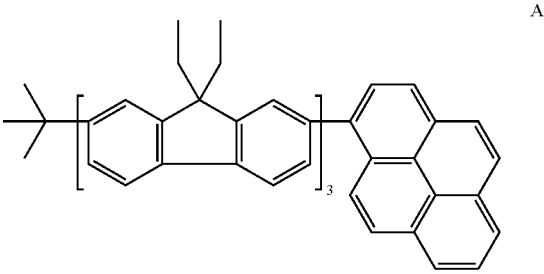
A-69
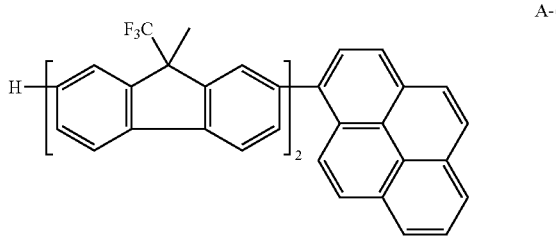
A-70
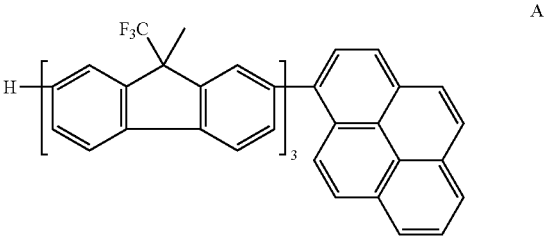

-continued
A-71
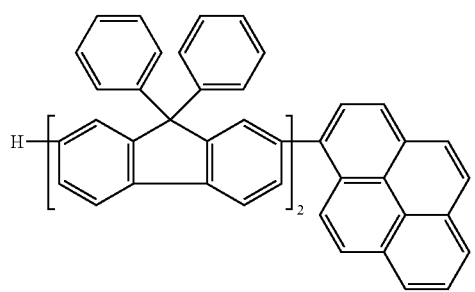
A-72
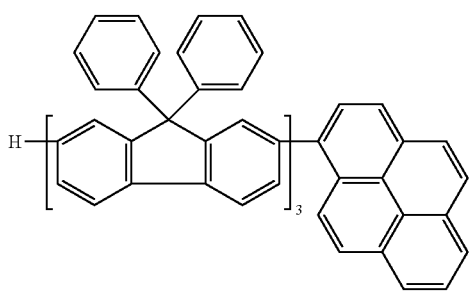
A-73
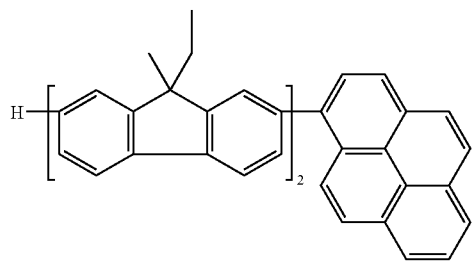
A-74
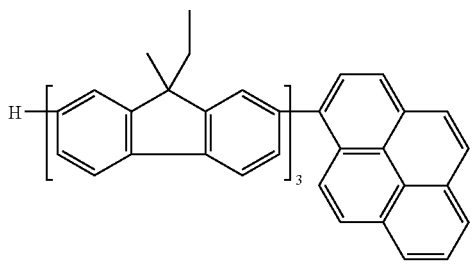
A-75
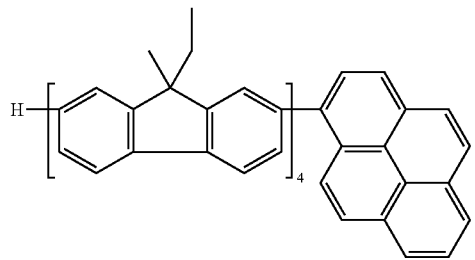
A-76
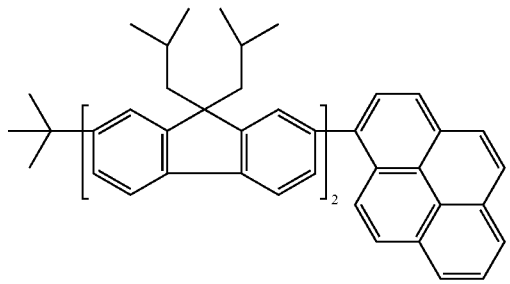
A-77
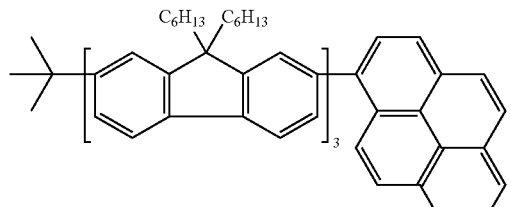
A-78
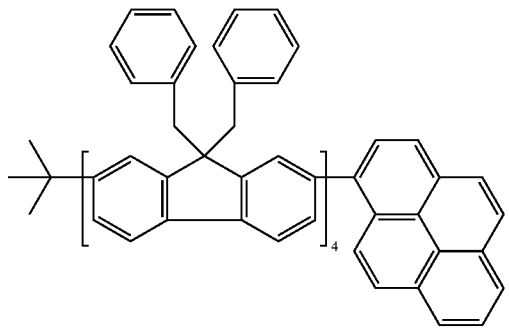
A-79
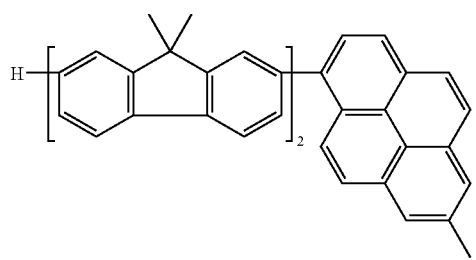
A-80
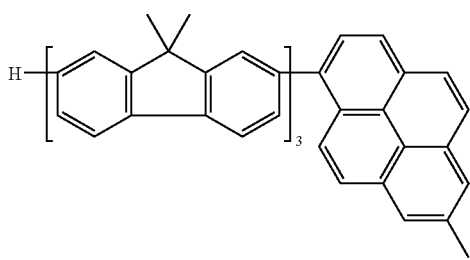

-continued
A-81
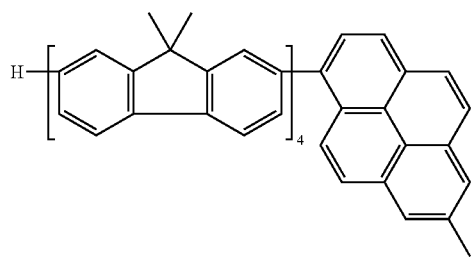
A-82
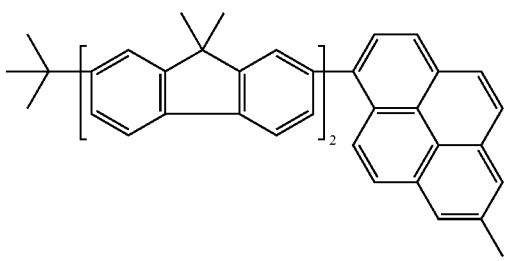
A-83
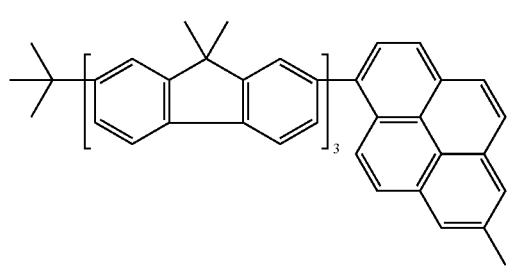
A-84
A-85
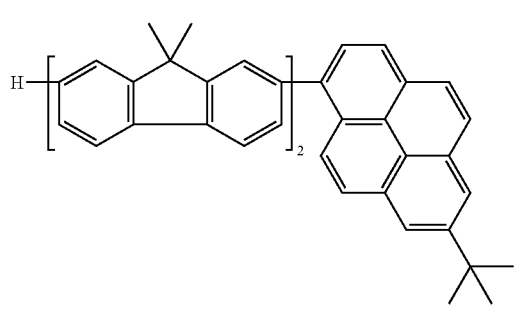
A-86
A-87
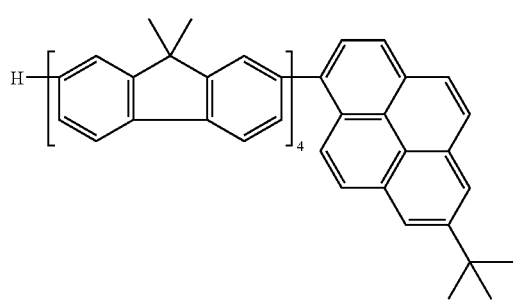
A-88
A-89
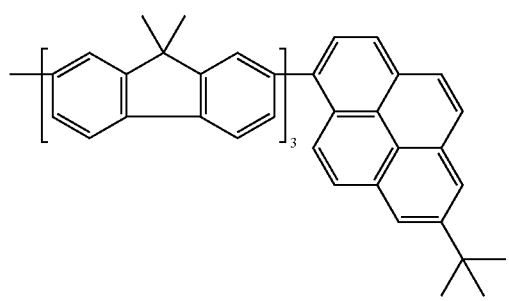
A-90
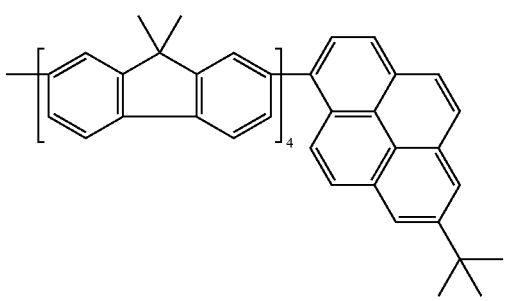

-continued
A-91
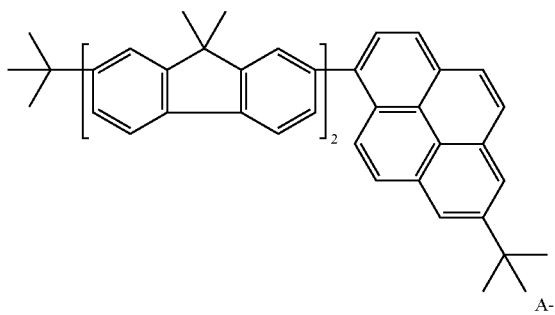
A-92
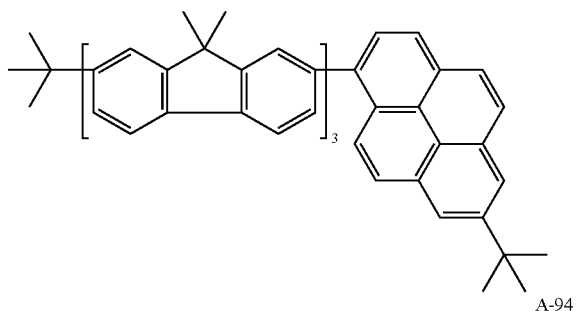
A-93
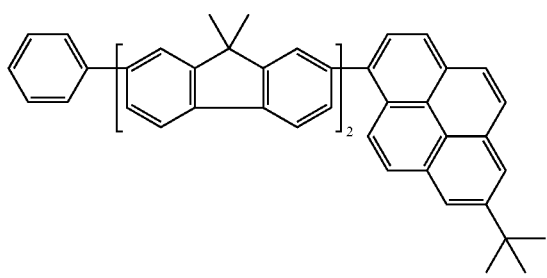
A-94
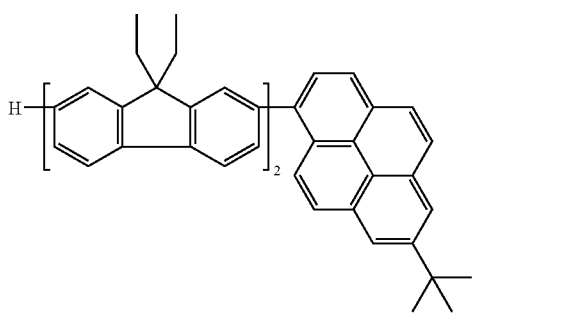
A-95
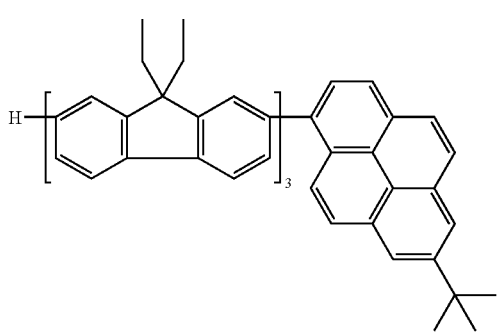
A-96
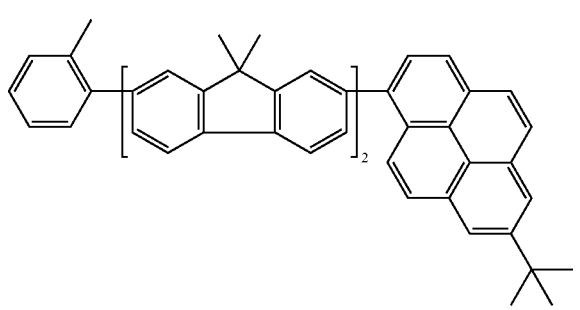
A-97
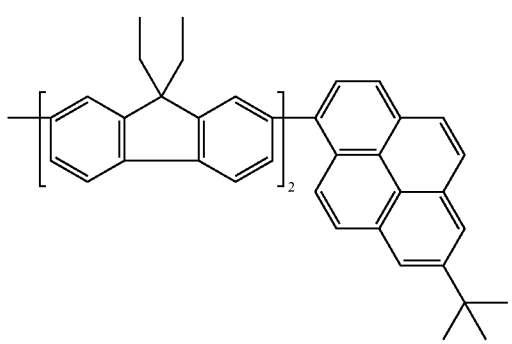
A-98
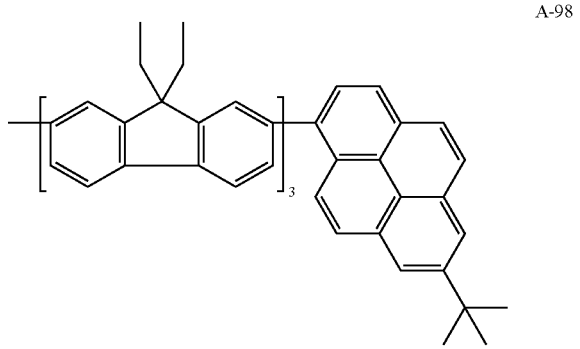
A-99
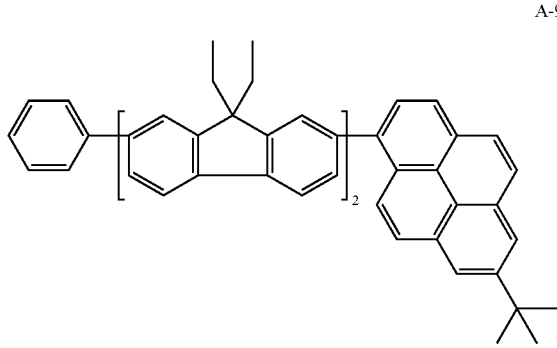
A-100
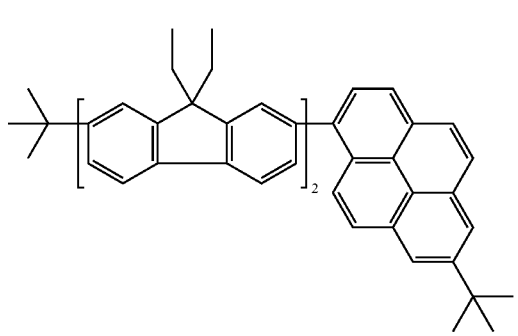

-continued
A-101
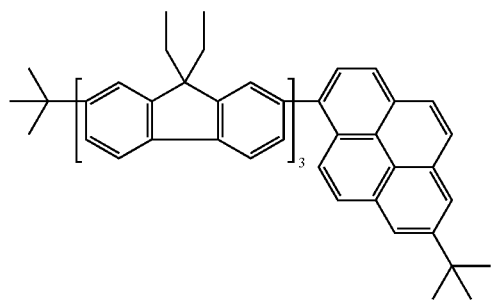
A-102
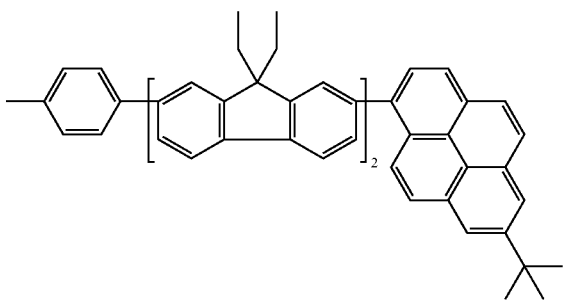
A-103
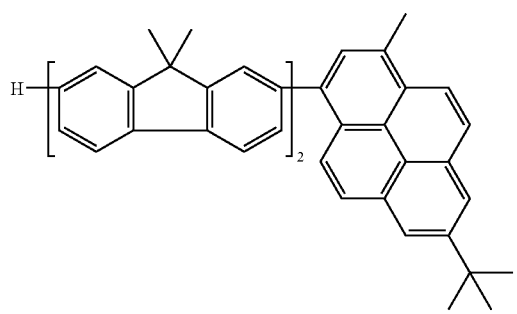
A-104
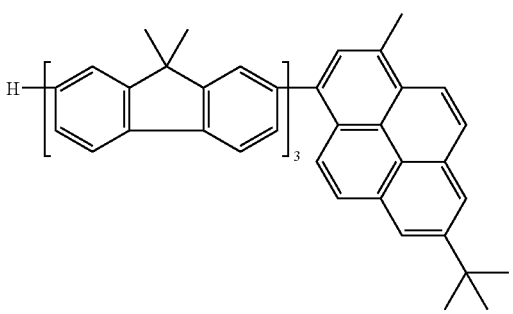
A-105
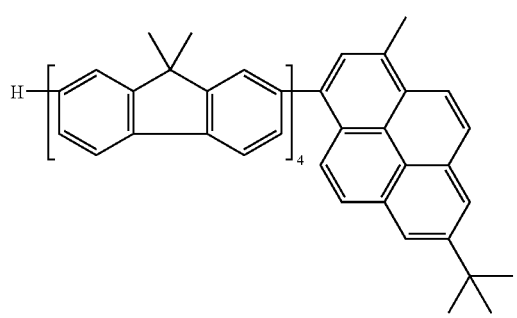
A-106
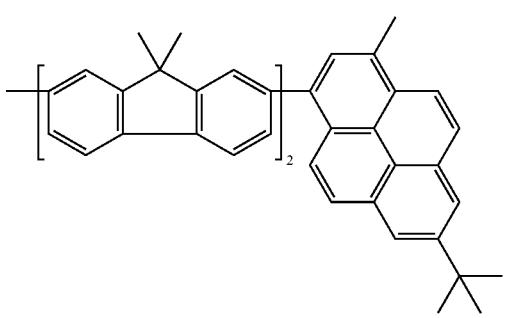
A-107
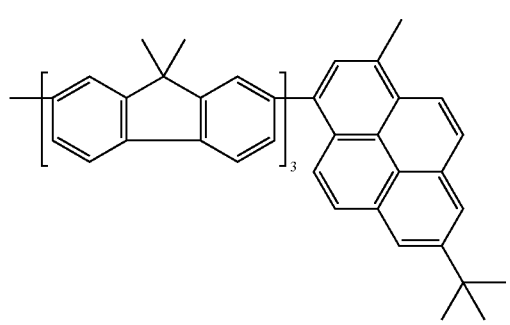
A-108
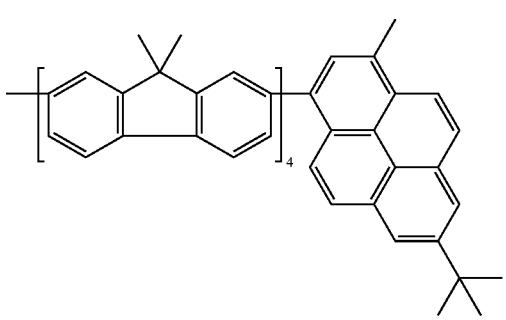
A-109
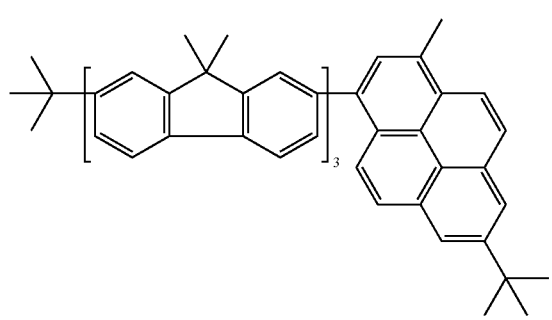
A-110
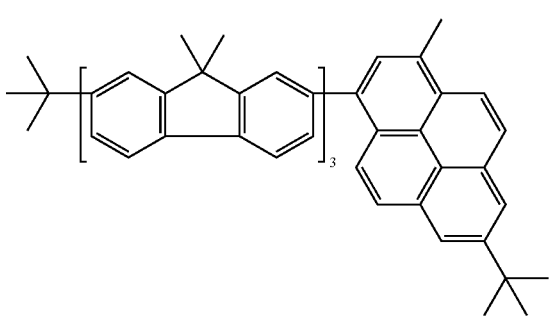

-continued
A-111
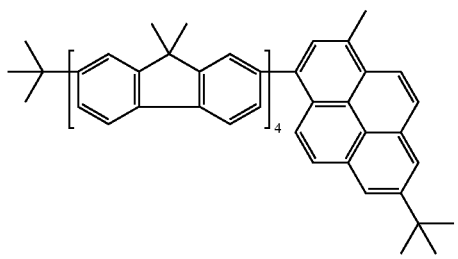
A-112
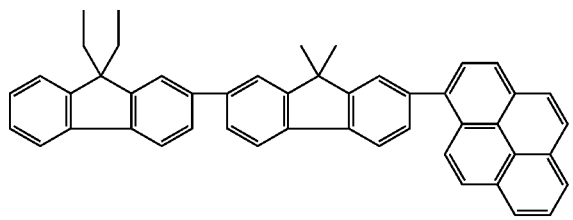
A-113
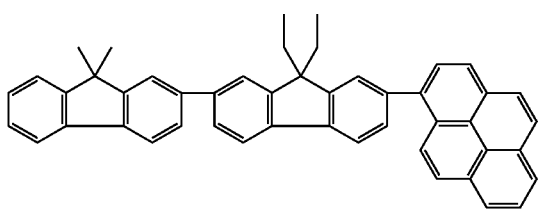
A-114
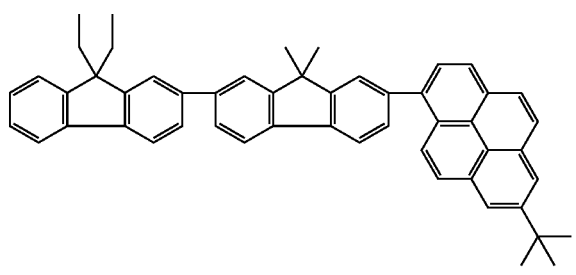
A-115
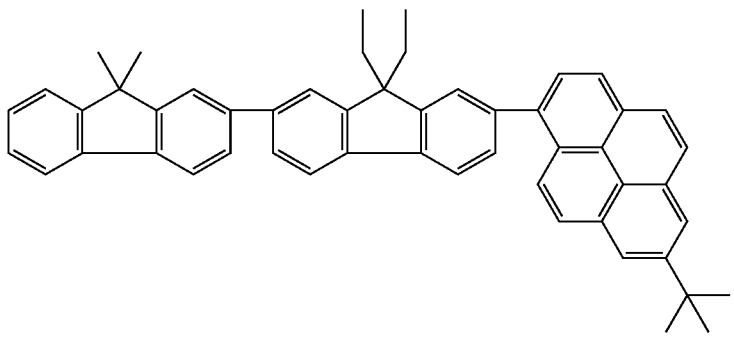
A-116
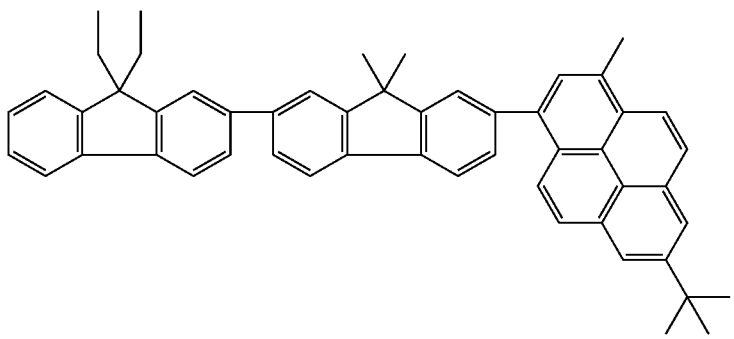
A-117
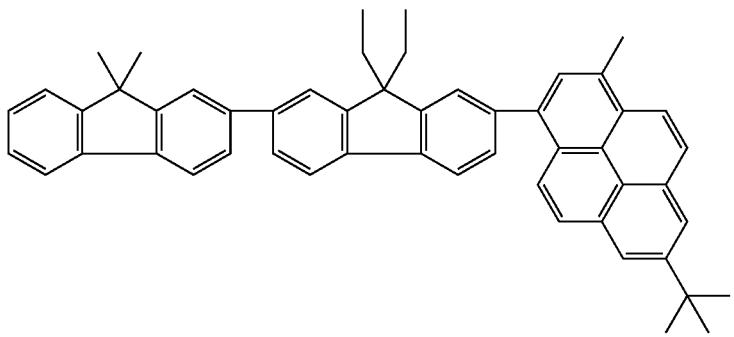

-continued
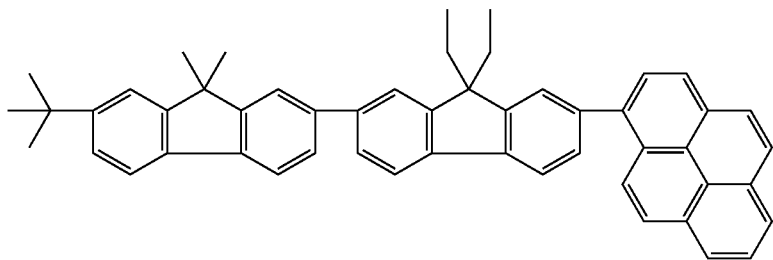
A-118
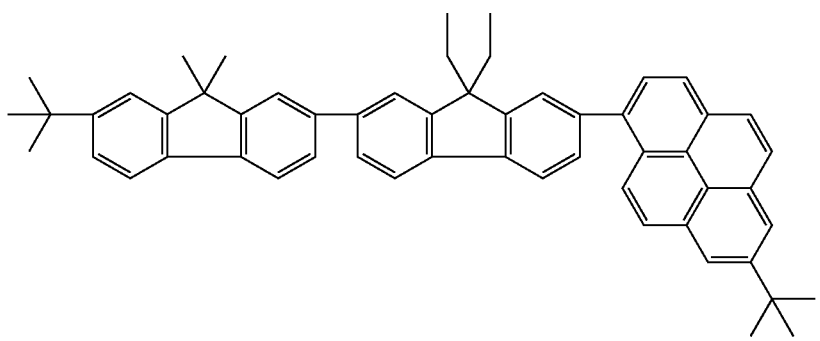
A-119
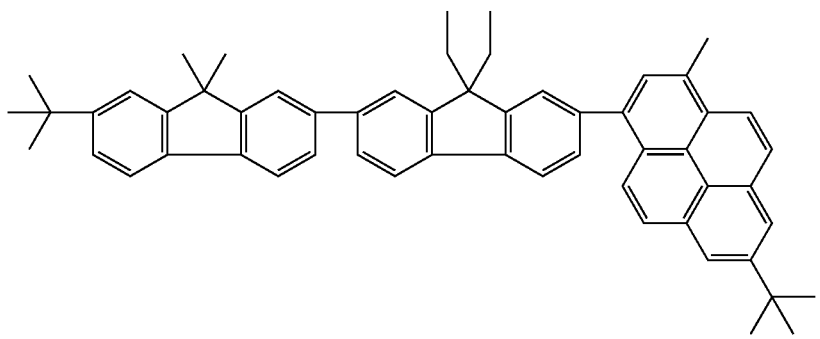
A-120
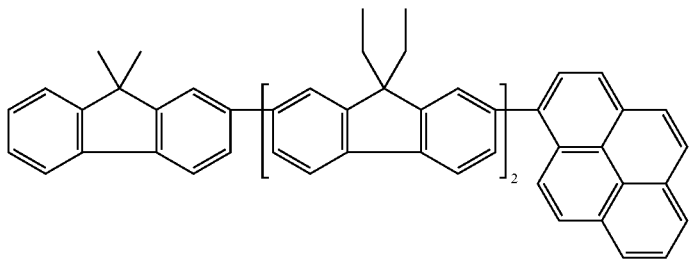
A-121
A-122
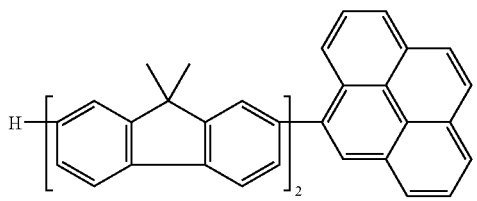
A-123
A-124
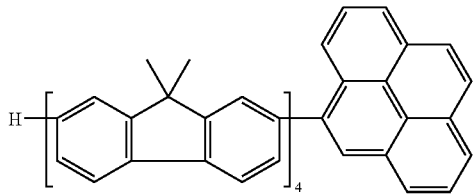
A-125
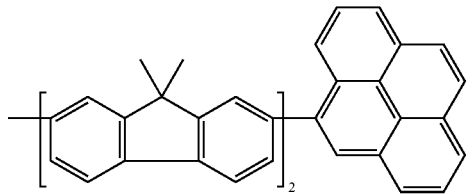

-continued
A-126
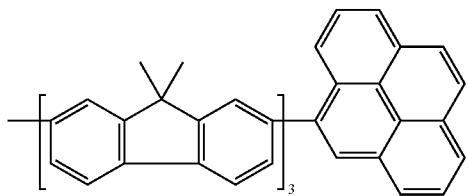
A-127
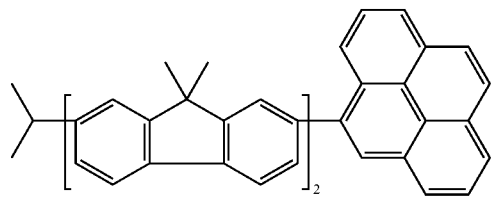
A-128
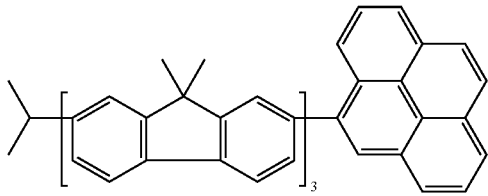
A-129
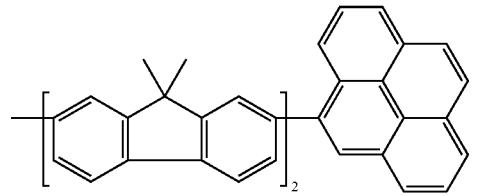
A-130
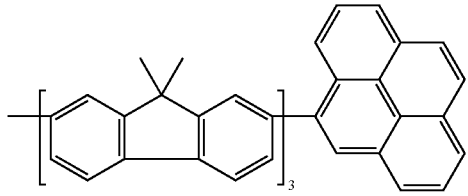
A-131
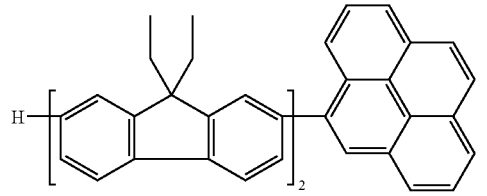
A-132
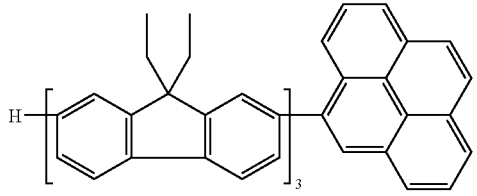
A-133
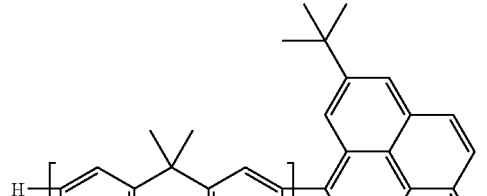
A-134
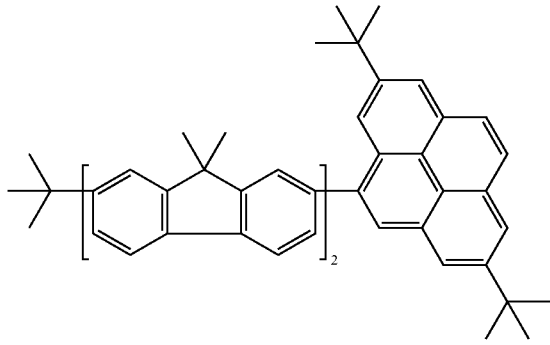
A-135
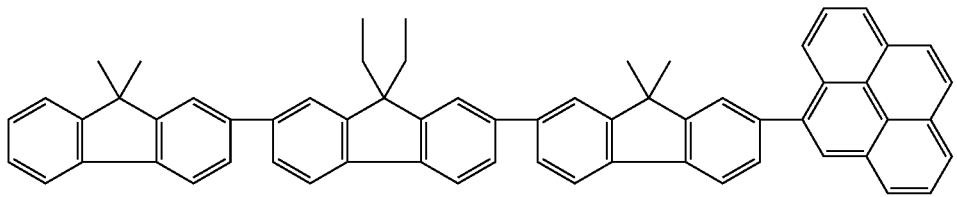

-continued
B-1
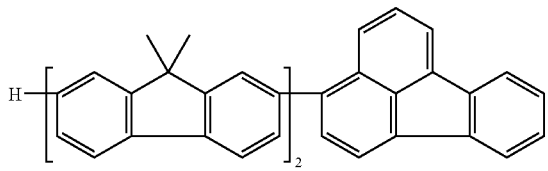
B-2
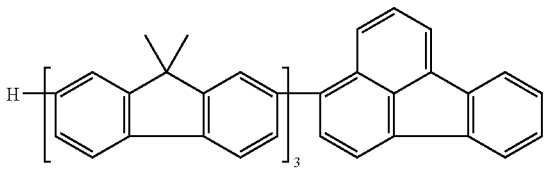
B-3
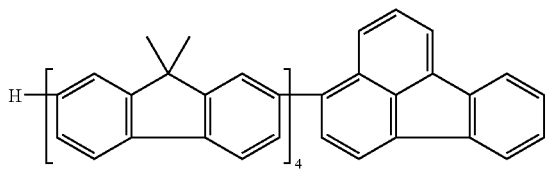
B-4
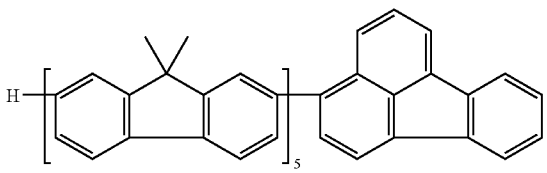
B-5
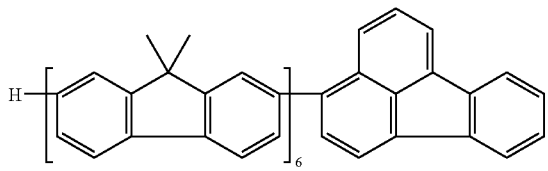
B-6
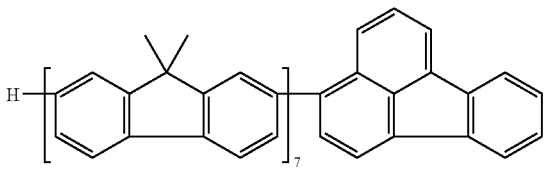
B-7
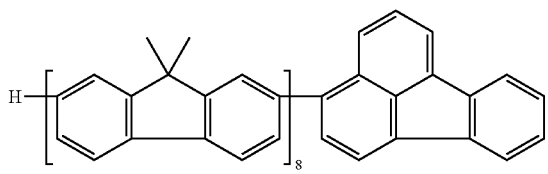
B-8
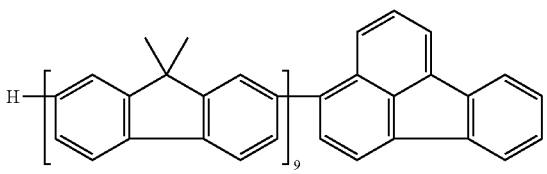
B-9
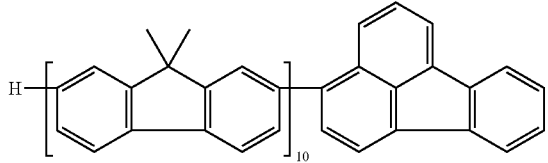
B-10
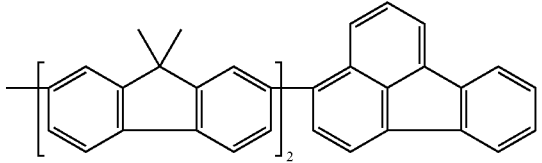
B-11
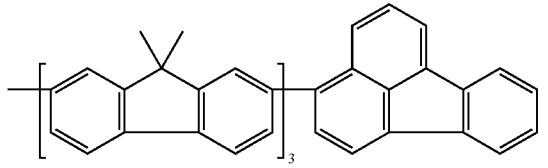
B-12
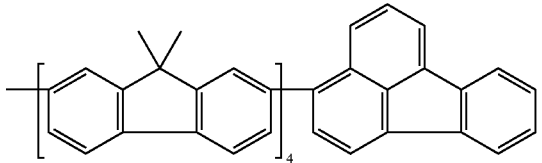
B-13
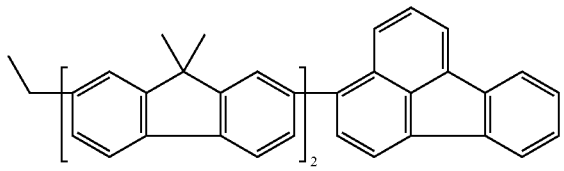
B-14
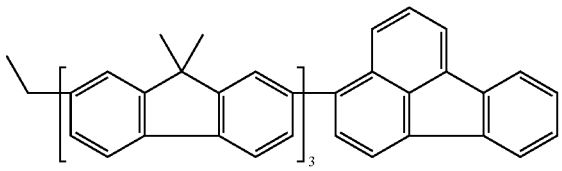
B-15
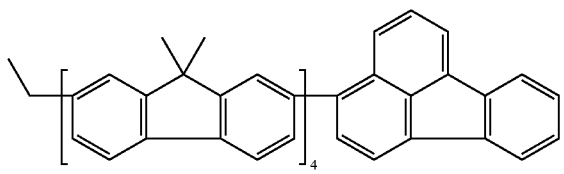
B-16
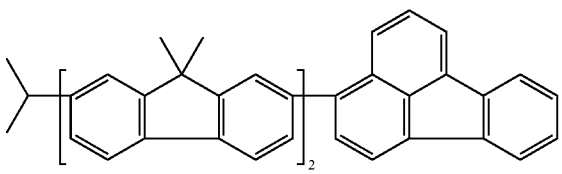

-continued
B-17
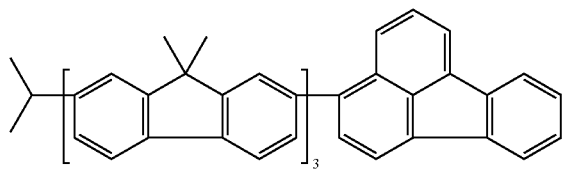
B-18
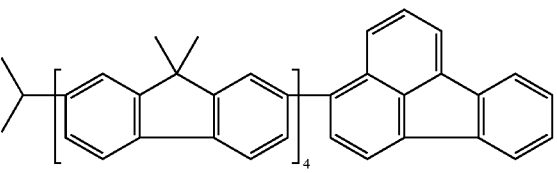
B-19
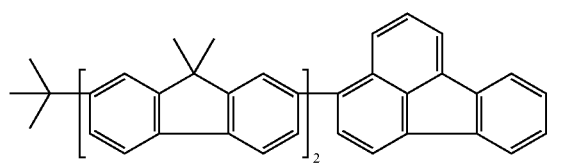
B-20
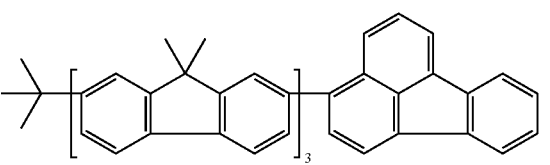
B-21
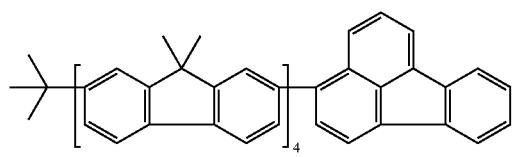
B-22
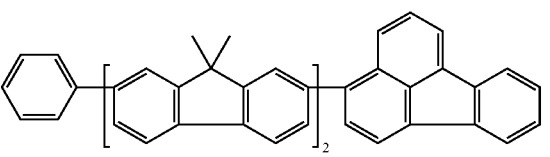
B-23
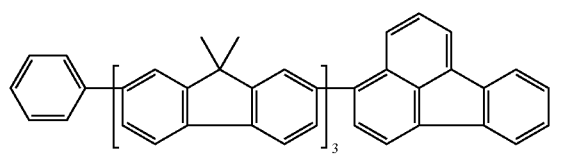
B-24
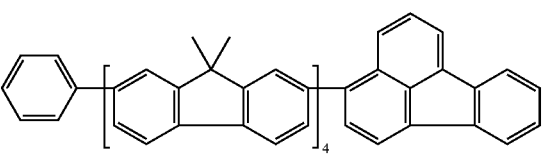
B-25
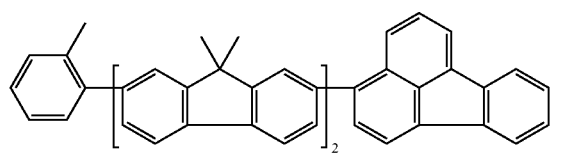
B-26
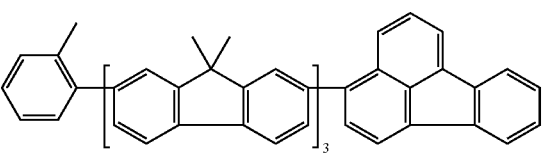
B-27
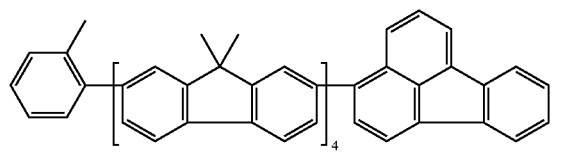
B-28
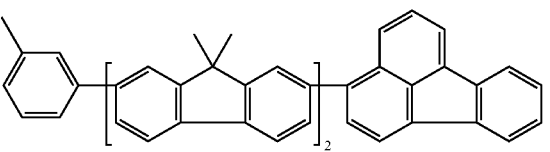
B-29
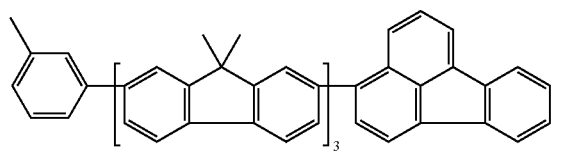
B-30
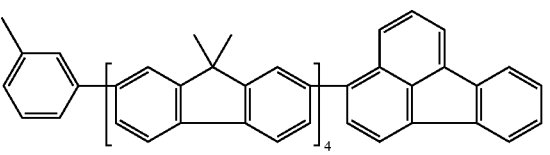
B-31
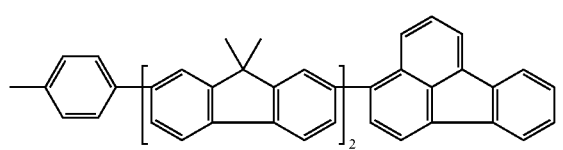
B-32
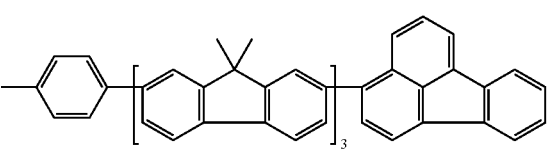

-continued

-continued
B-49
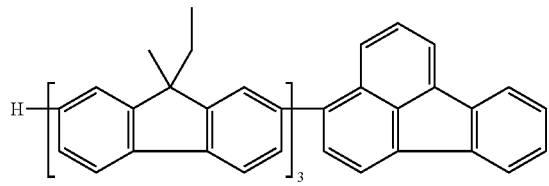
B-50
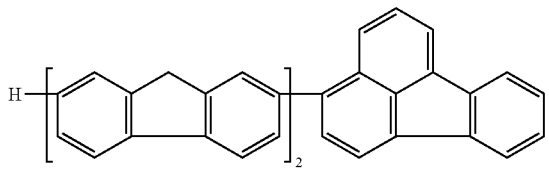
B-51
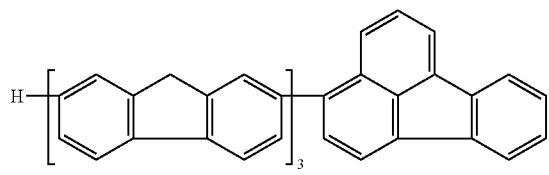
B-52
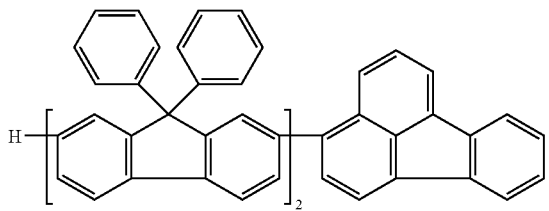
B-53
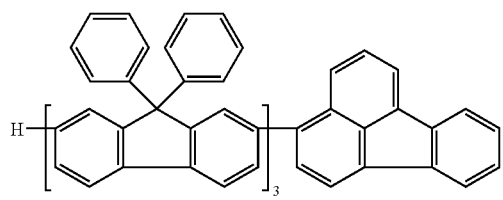
B-54
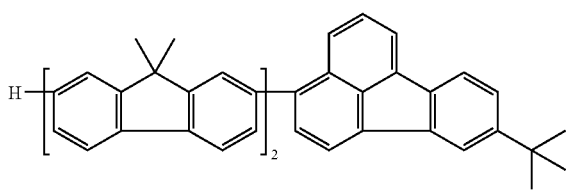
B-55
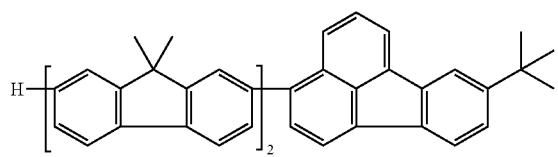
B-56
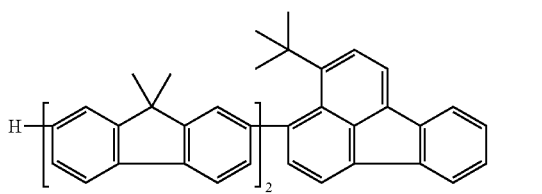
B-57
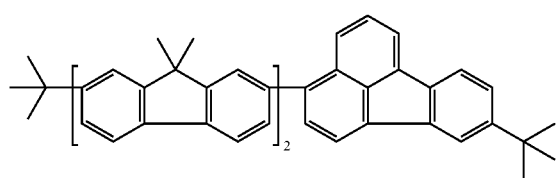
B-58
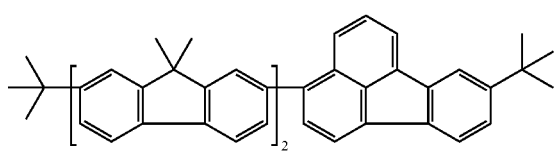
B-59
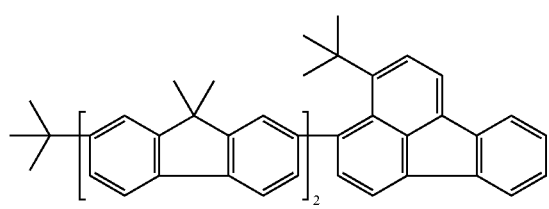
B-60
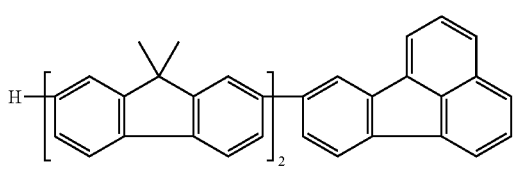
B-61
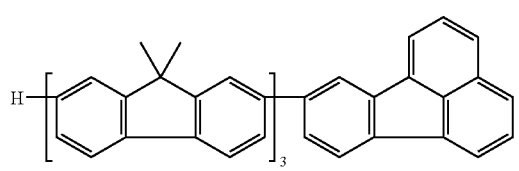
B-62

-continued
B-63 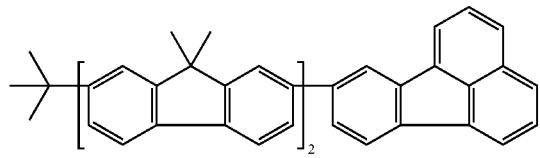
B-65 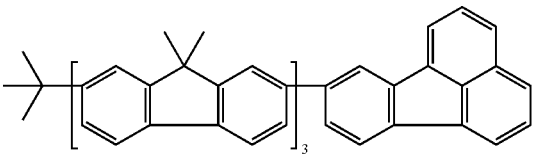
B-65 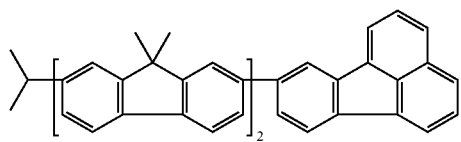
B-66 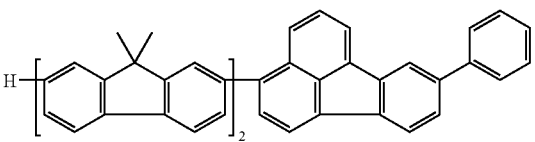
B-67 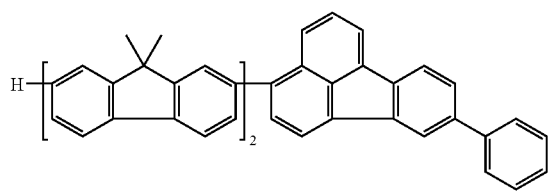
B-68 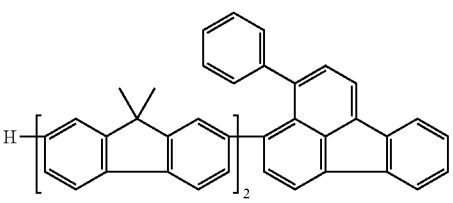
C-1 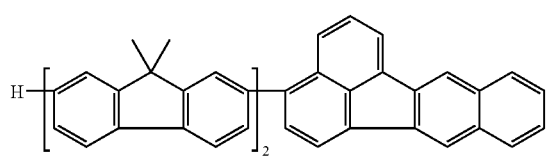
C-2 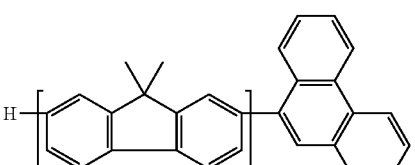
C-3 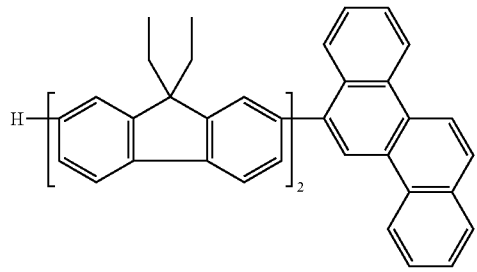
C-4 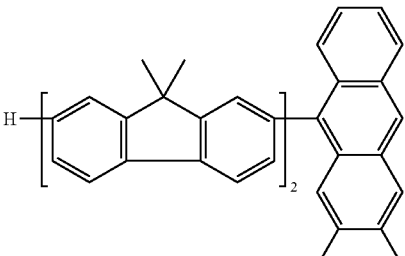
C-5 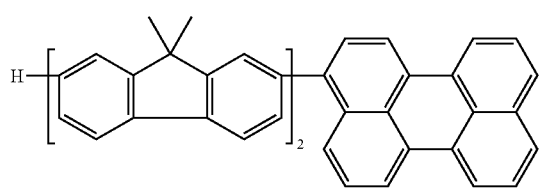
C-6 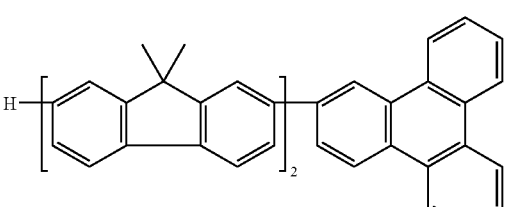
C-7 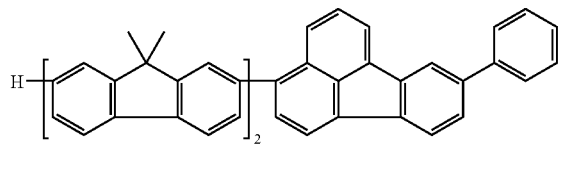
C-8 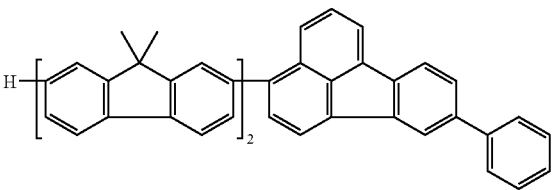

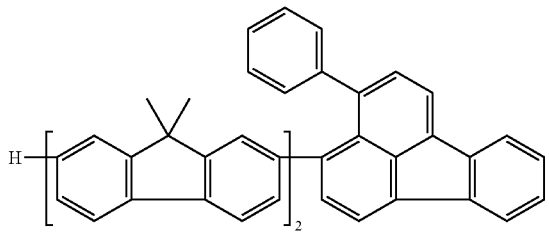

C-9

Next, the organic light-emitting device of the present invention will be described in detail below.

The organic light-emitting device of the present invention comprises a pair of electrodes including an anode and a cathode, and a layer comprising an organic compound provided between the pair of electrodes, wherein the layer comprising the organic compound comprises at least one of the compounds represented by the general formula (I).

In the organic light-emitting device of the present invention, it is preferred that at least a light-emitting layer of layer(s) containing organic compound(s) contains at least one of the compounds represented by the general formula (I).

Further, it is also preferred that in an organic light-emitting device with a light-emitting layer comprising two or more kinds of compounds of a host and a guest, the host or the guest is the compound represented by the general formula (I). Incidentally, the term "guest" herein employed refers to a compound which emits light in response to recombination of holes and electrons in a light-emitting region of an organic electroluminescence (EL) device and is contained in a substance (host) for forming the light-emitting region.

When the compound represented by the general formula (I) according to the present invention is used as a guest, the content thereof is preferably 50 wt. % or less, more preferably 0.1 wt. % or more and 30 wt. % or less, and most preferably 0.1 wt. % or more and 15 wt. % or less.

On the other hand, when the compound represented by the general formula (I) according to the present invention is used as a host compound, the guest compound is not particularly limited, and the compounds described later can suitably be selected and used depending on the desired emission color and the like. Further, in addition to the doping with the guest, the host material may also be doped with a hole-transporting compound, an electron-transporting compound or the like as needed.

The compound of the present invention may be used only for a light-emitting layer as an organic compound layer, but may also be used, besides the light-emitting layer, for a hole injection layer, a hole-transporting layer, an electron injection layer, an electron-transporting layer, an electron-blocking layer, or the like as needed.

In the organic light-emitting device of the present invention, a layer containing the compound represented by the general formula (I) is formed by a method such as vacuum deposition or solution coating between an anode and a cathode. It is preferred that the organic layer is formed in a thin film with a thickness of generally 10 μm or less, preferably 0.5 μm or less, and more preferably 0.01 μm or more and 0.5 μm or less.

FIGS. 1 to 6 illustrate preferable examples of the organic light-emitting device according to the present invention.

First, the reference numerals in the figures will be explained.

Reference numeral 1 denotes a substrate, reference numeral 2 denotes an anode, reference numeral 3 denotes a light-emitting layer, reference numeral 4 denotes a cathode, reference numeral 5 denotes a hole-transporting layer, reference numeral 6 denotes an electron-transporting layer, reference numeral 7 denotes a hole injection layer, and reference numeral 8 denotes a hole/exciton blocking layer.

FIG. 1 is a cross-sectional view showing an example of the organic light-emitting device according to the present invention. In FIG. 1, the device has a configuration in which an anode 2, a light-emitting layer 3, and a cathode 4 are provided sequentially on a substrate 1. A light-emitting device with this configuration is advantageous when the light-emitting material itself has all of hole transportability, electron transportability, and light-emitting property, or when compounds, respectively, having these characteristics are used in combination.

Figure 2:
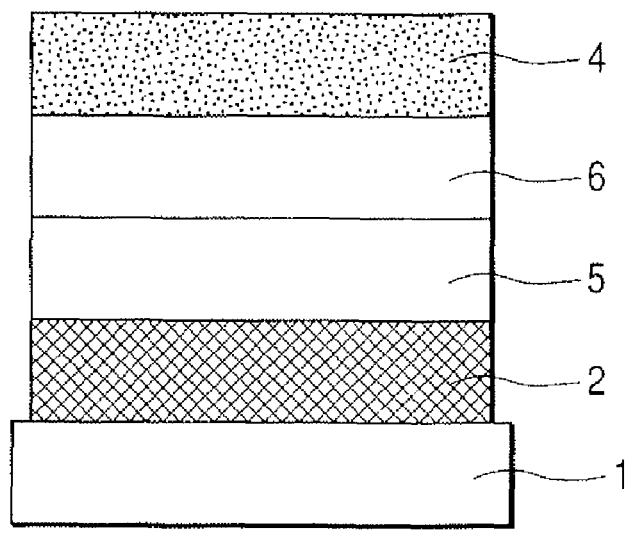
FIG. 2 is a schematic cross-sectional view showing another example of the organic light-emitting device in accordance with the present invention.

FIG. 2 is a cross-sectional view showing another example of the organic light-emitting device according to the present invention. In FIG. 2, the device has a configuration such that an anode 2, a hole-transporting layer 5, an electron-transporting layer 6, and a cathode 4 are formed sequentially on a substrate 1. A light-emitting device with this configuration is advantageous when a light-emitting material having either or both of hole transportability and electron transportability is used for the respective layers, in combination with a hole-transporting material having no light-emitting property or an electron-transporting material having no light-emitting property. In addition, in this case, either one of the hole-transporting layer 5 and the electron-transporting layer 6 also serves as the light-emitting layer.

Figure 3:
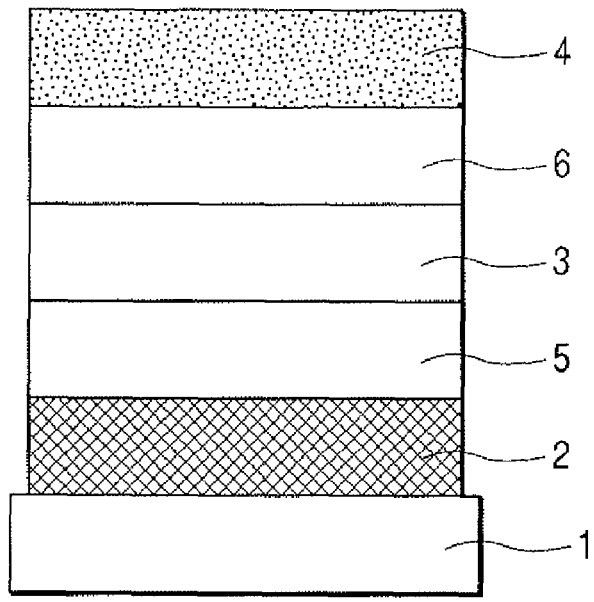
FIG. 3 is a schematic cross-sectional view showing still another example of the organic light-emitting device in accordance with the present invention.

FIG. 3 is a cross-sectional view showing still another example of the organic light-emitting device according to the present invention. In FIG. 3, the device has a configuration in which an anode 2, a hole-transporting layer 5, a light-emitting layer 3, an electron-transporting layer 6, and a cathode 4 are formed sequentially on a substrate 1. With this configuration, the carrier-transporting function and the light-emitting function are separated from each other. That is, compounds, respectively, having hole-transporting property, electron-transporting property, and light-emitting property can be used appropriately in combination. As a result, the degree of freedom in selecting materials greatly increases, and various kinds of compounds having different emission wavelengths can be used, whereby a variety of emission wavelengths can be achieved.

Furthermore, it also becomes possible to effectively confine carriers or excitons in the light-emitting layer at the middle portion, to thereby increase the emission efficiency.

Figure 4:
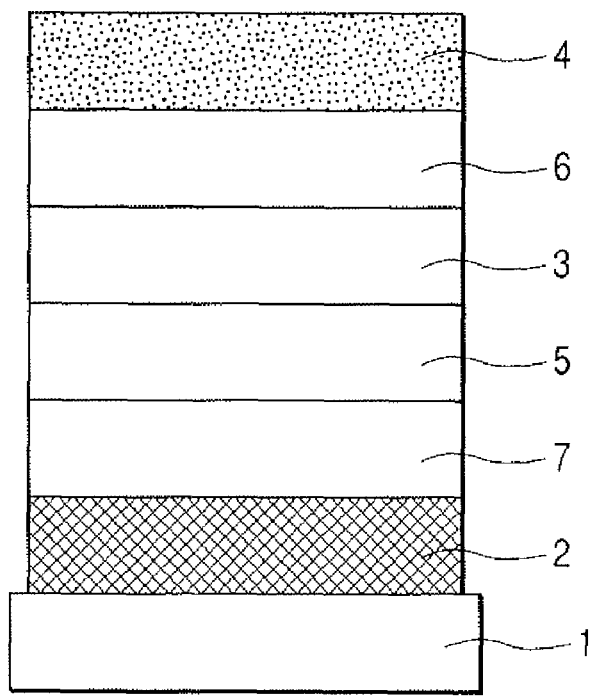
FIG. 4 is a schematic cross-sectional view showing yet another example of the organic light-emitting device in accordance with the present invention.

FIG. 4 is a cross-sectional view showing still another example of the organic light-emitting device according to the present invention. In FIG. 4, as compared with FIG. 3, the device is constructed such that a hole injection layer 7 is provided on the anode side, which is effective for improving adhesion between the anode and the hole-transporting layer or improving the hole injection property, thus being effective for reducing the driving voltage.

Figure 5:
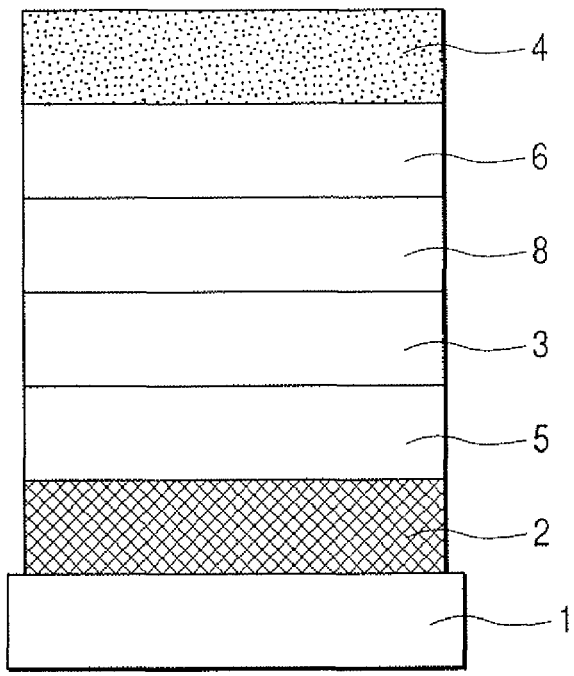
FIG. 5 is a schematic cross-sectional view showing yet still another example of the organic light-emitting device in accordance with the present invention.
Figure 6:
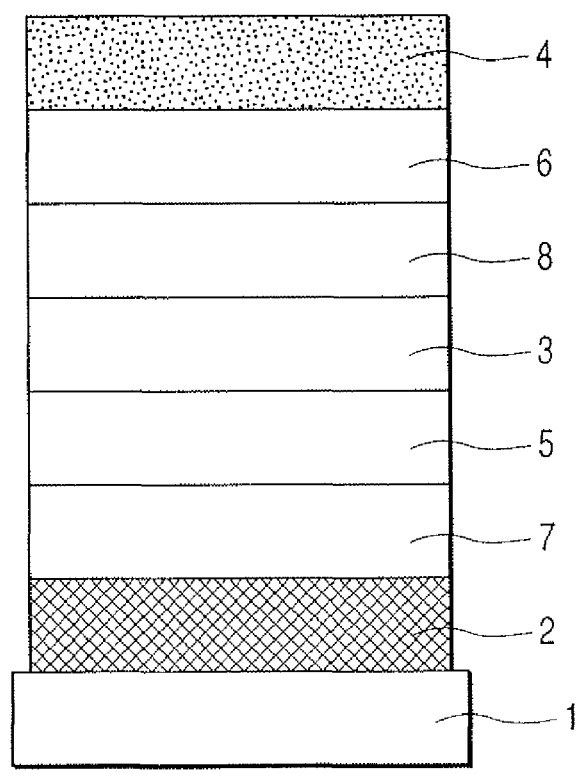
FIG. 6 is a schematic cross-sectional view showing yet again another example of the organic light-emitting device in accordance with the present invention.

FIGS. 5 and 6 are cross-sectional views showing yet still other examples of the organic light-emitting device according to the present invention. In each of FIGS. 5 and 6, as compared with FIGS. 3 and 4, the device is constructed such that a layer (a hole blocking layer 8) serving to prevent holes or excitons from passing through toward the cathode is provided between the light-emitting layer and the electron-transporting layer. Using a compound having an extremely high ionization potential for the hole blocking layer 8 is effective for improving the emission efficiency.

It is to be noted that FIGS. 1 to 6 merely show very basic device configurations, and that the structure of the organic light-emitting device using the compound according to the present invention is not limited thereto. For example, it is possible to adopt various layer configurations, such as one in which an insulating layer is provided at an interface between an electrode and an organic layer, one in which an adhesive layer or an interference layer is provided, or one in which a hole-transporting layer is composed of two layers with different ionization potentials.

The compound represented by the general formula (I) according to the present invention is superior in electron-transporting property, light-emitting property and durability than the conventional compounds and can be used in any one of the configurations illustrated in FIGS. 1 to 6.

In the present invention, the compound represented by the general formula (I) is used as a constituent for an electron-transporting layer and a light-emitting layer but can also be used in combination with a hitherto known hole-transporting compound, light-emitting compound, electron-transporting compound, or the like.

Examples of such compounds will be shown below.

<Hole-Transporting Compound>

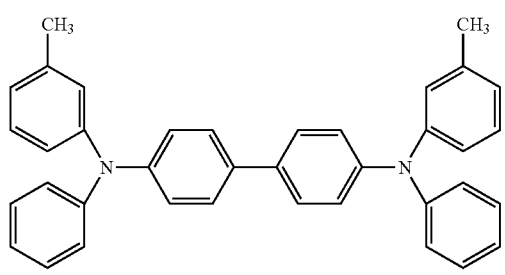

TPD

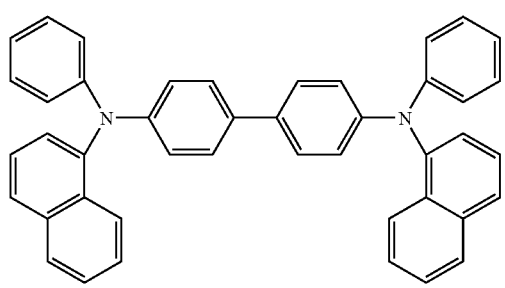

a-NPD

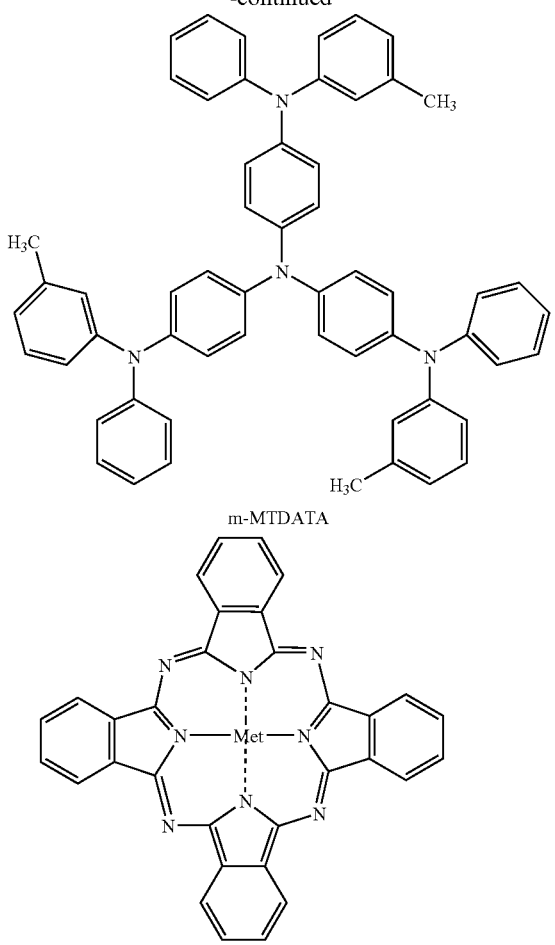

m-MTDATA

Met: Cu, Mg, AlCl, TiO, SnCl2 etc.
Met-Pc

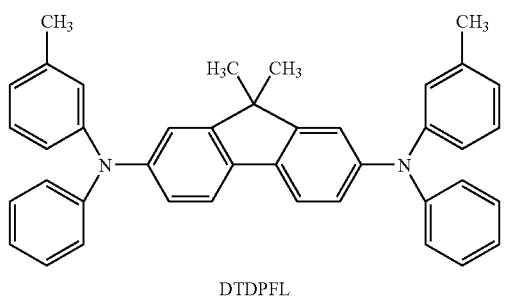

DTDPFL

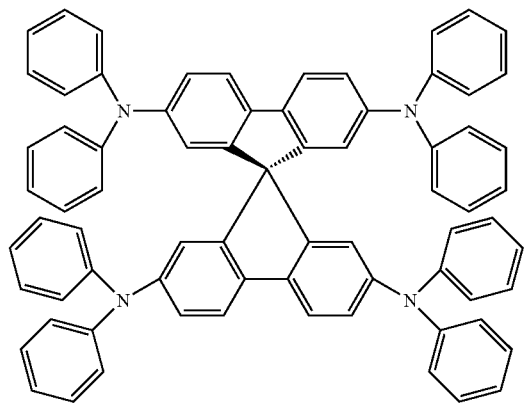

spiro-TPD

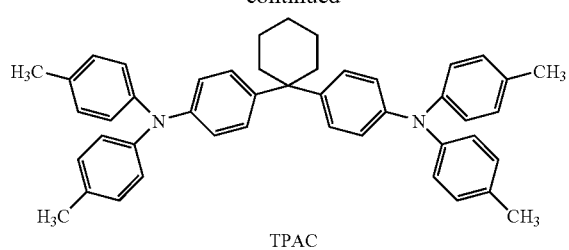
TPAC
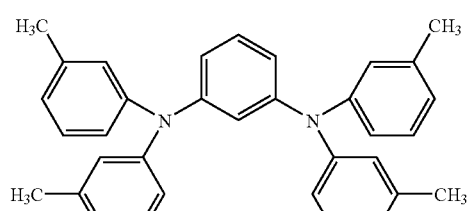
PDA
<Electron-Transporting, Light-Emitting Compound>
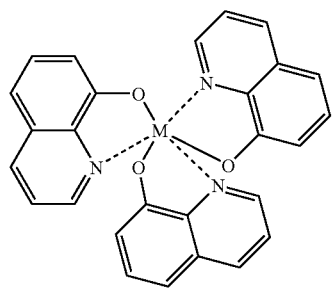
M: Al, Ga
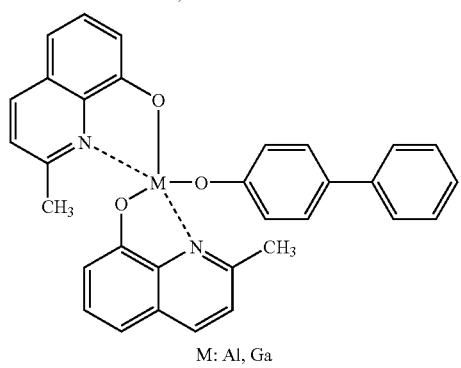
M: Al, Ga
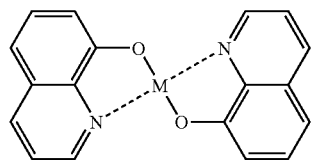
M: Zn, Mg, Be
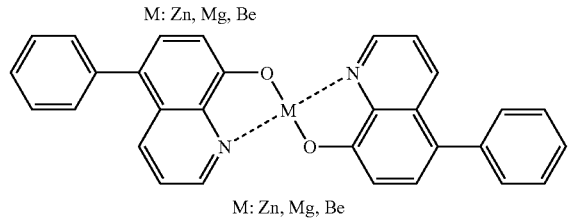
M: Zn, Mg, Be
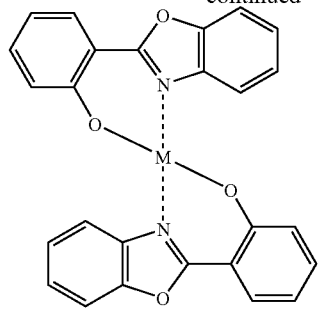
M: Zn, Mg, Be
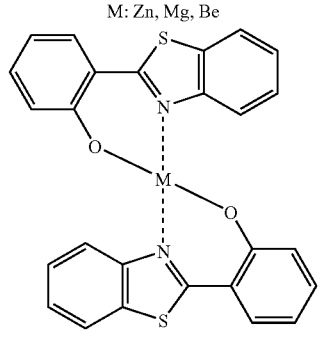
M: Zn, Mg, Be
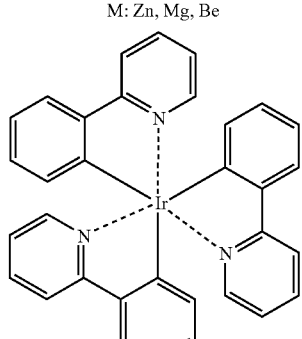
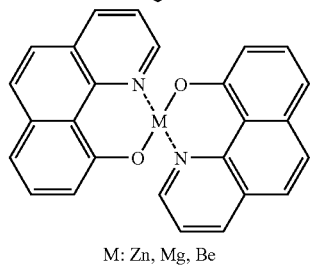
M: Zn, Mg, Be
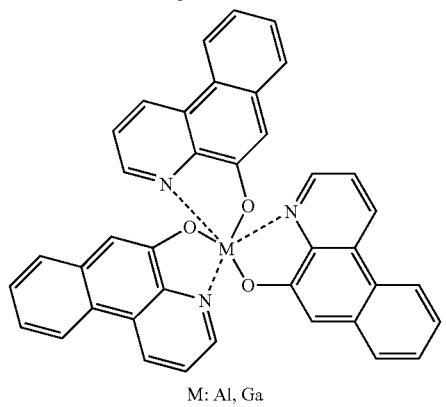
M: Al, Ga <Light-Emitting Compound>
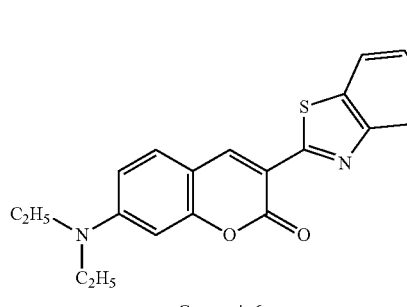
Coumarin6
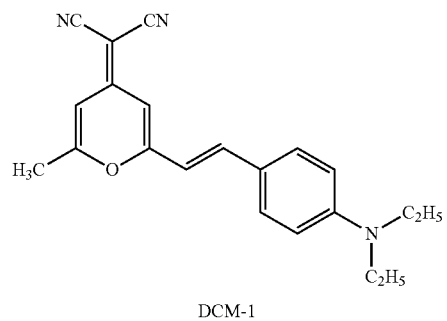
DCM-1
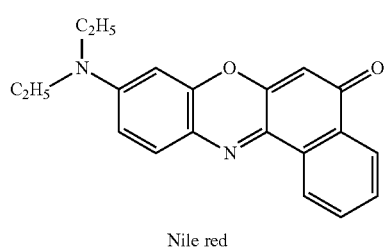
Nile red
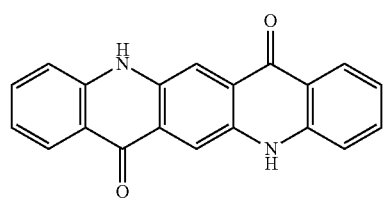
Quinacridone
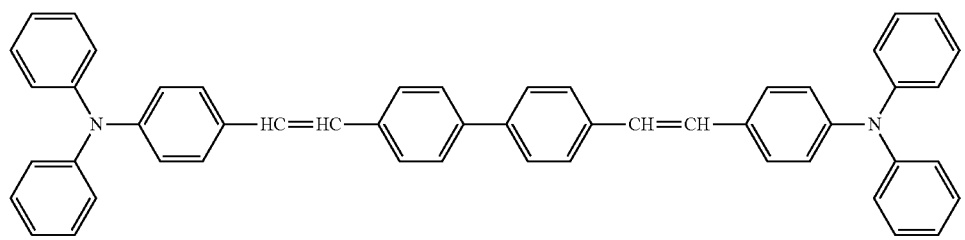
DPABVi
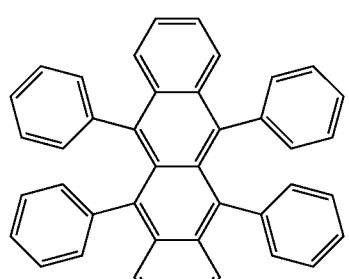
Rubrene
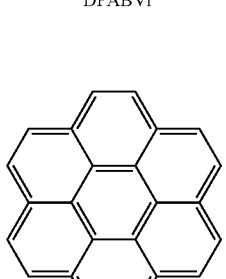
Coronene
<Light-Emitting Layer Matrix Compound And Electron-Transporting Compound>
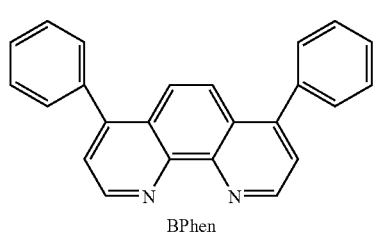
BPhen
-continued
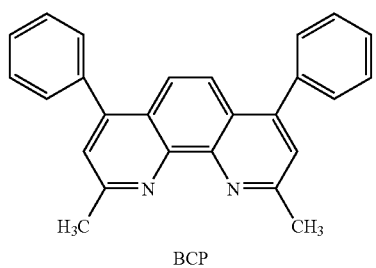
BCP -continued
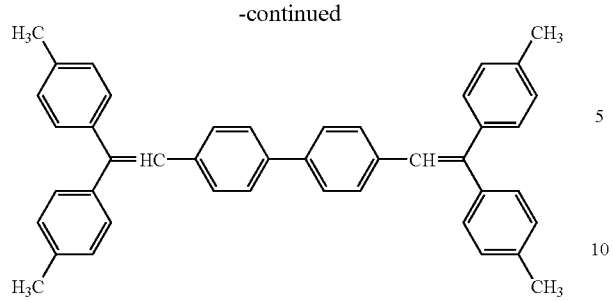
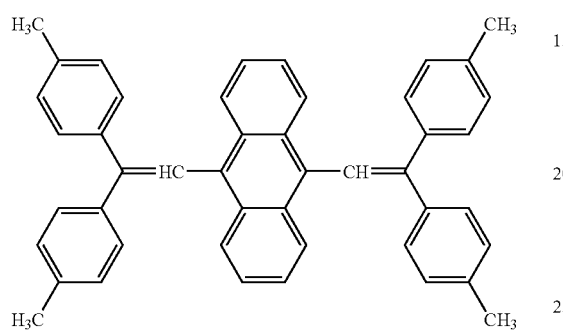
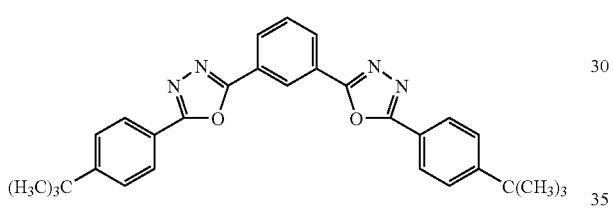
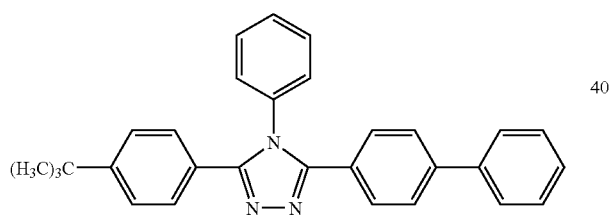
-continued
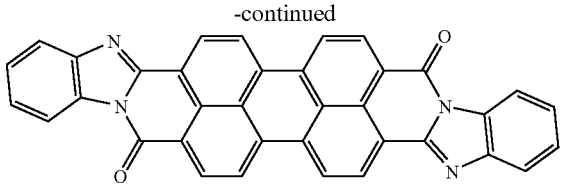
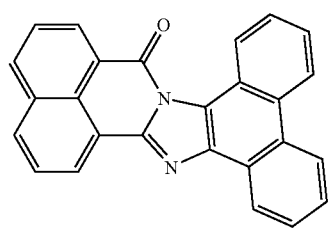
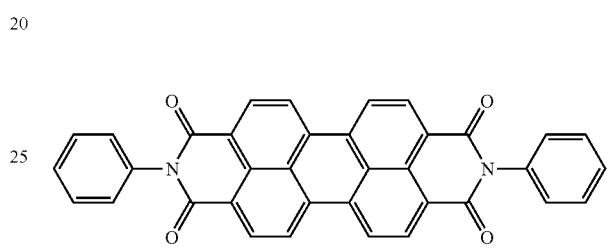
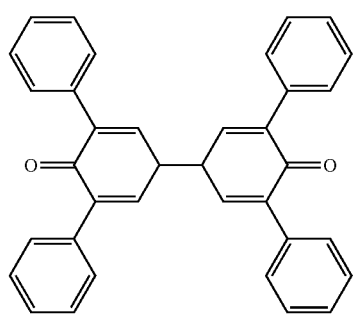
<Polymeric Hole-Transporting Compound>
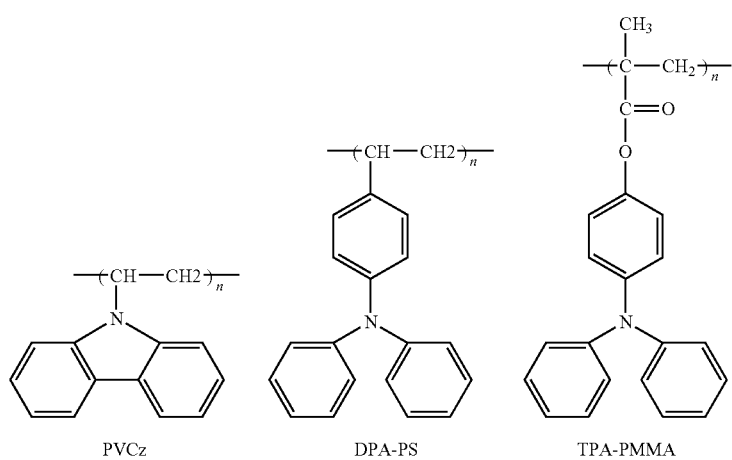
PVCz     DPA-PS     TPA-PMMA -continued
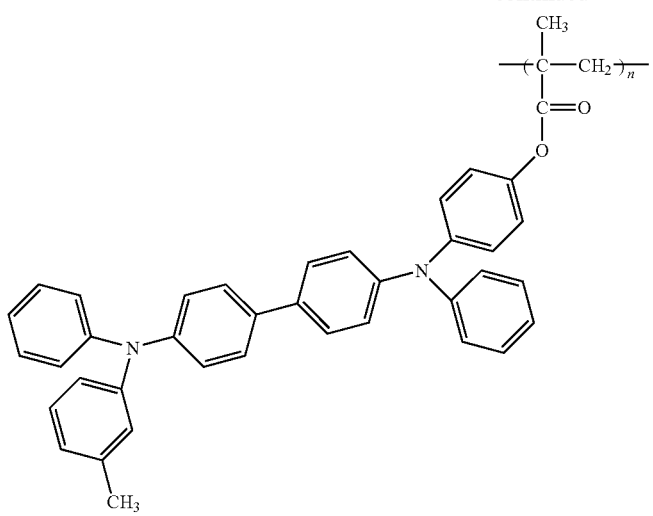
TPD-PMMA
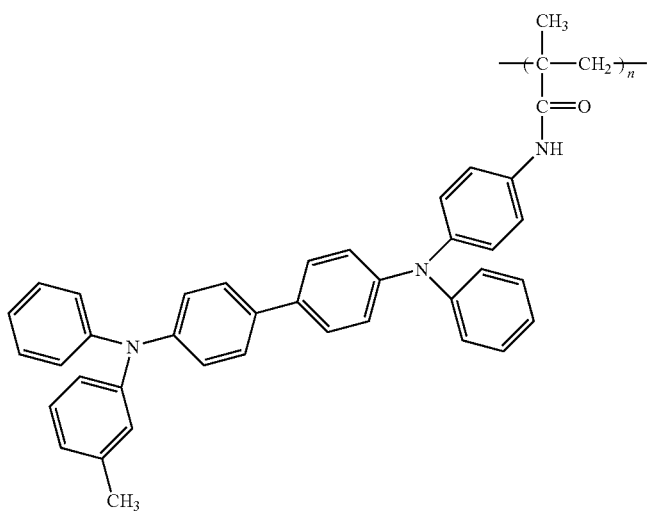
TPD-PMMA
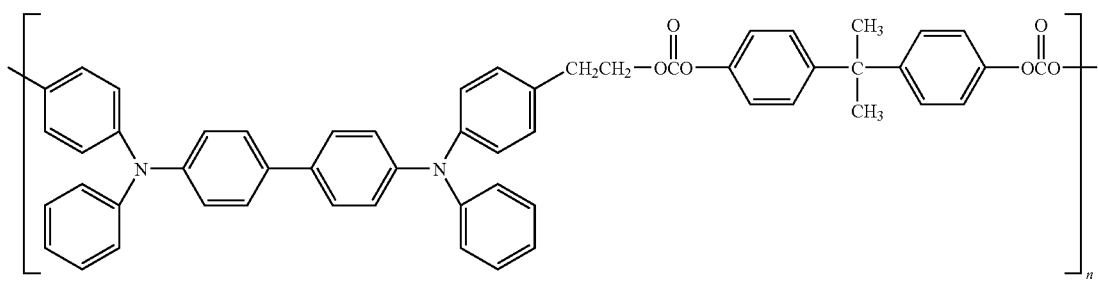
TPD-PCA
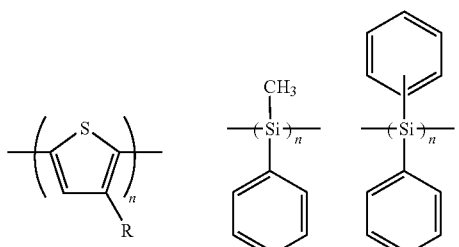
R: C6H13, C8H17, C12H25
Polythiophene    Polysilicone <Polymeric Light-Emitting Compound and Charge-Transporting Compound>

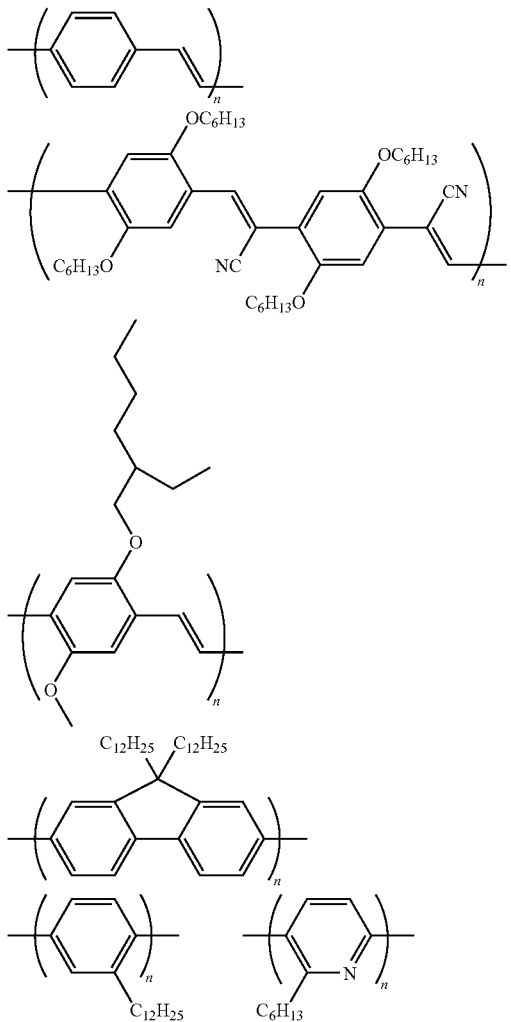

In the organic light-emitting device of the present invention, the layer containing the compound represented by the general formula (I) and the other layers comprising an organic compound are formed as a thin film generally by using a vacuum deposition method or a coating method of applying such organic compound dissolved in a suitable solvent. Particularly, when the film is formed by the coating method, the film can be formed by additionally using a suitable binder resin.

The above-mentioned binder resin can be selected from a wide range of binding resins, and includes, for instance, polyvinylcarbazole resin, polycarbonate resin, polyester resin, polyarylate resin, polystyrene resin, acrylic resin, methacrylic resin, butyral resin, polyvinylacetal resin, diallylphthalate resin, phenolic resin, epoxy resin, silicone resin, polysulfonic resin and urea resin, but is not limited thereto. In addition, the binder resin may be singly used, or be used in combination as a copolymer.

An anode material used preferably has as large a work function as possible, and includes, for instance, an elemental metal such as gold, platinum, nickel, palladium, cobalt, selenium, and vanadium, an alloy thereof, and a metal oxide such as stannic oxide, zinc oxide, indium tin oxide (ITO) and indium zinc oxide. Further, a conductive polymer such as polyaniline, polypyrrole, polythiophene, and polyphenylene sulfide can be employed. These electrode materials can be used singly or in combination.

On the other hand, a cathode material used preferably has a low work function, and includes, for instance an elemental metal such as lithium, sodium, potassium, cesium, calcium, magnesium, aluminum, indium, silver, lead, tin, and chromium; or an alloy made of a plurality of the above metals. A metal oxide such as indium tin oxide (ITO) can be also used. In addition, the cathode may be either of a single layer configuration or of a multilayer configuration.

A substrate used in the present invention is not particularly limited, but an opaque substrate such as a metal substrate and a ceramic substrate or a transparent substrate such as glass, quartz, and a plastic sheet is used. Further, it is also possible to employ, for a substrate, a color filter film, a fluorescent color conversion filter film and a dielectric reflective film to thereby control the emission color.

Incidentally, after a device has been produced, a protective layer or an encapsulation layer may further be provided, for the purpose of preventing contact with oxygen or moisture. Examples of such a protective layer include a diamond thin film; a film of an inorganic material such as a metal oxide and a metal nitride; a film of a polymer such as a fluororesin, poly-p-xylene, polyethylene, silicone resin, and polystyrene resin; and further a film of a photocurable resin. Further, the produced device may also be covered with glass, a gas-impermeable film and a metal, or be packaged with a suitable encapsulation resin.

EXAMPLES

The present invention will be now described more in detail below with reference to examples, but the present invention is not limited to the examples.

Example 1

Synthesis of Exemplary Compound No. A-85

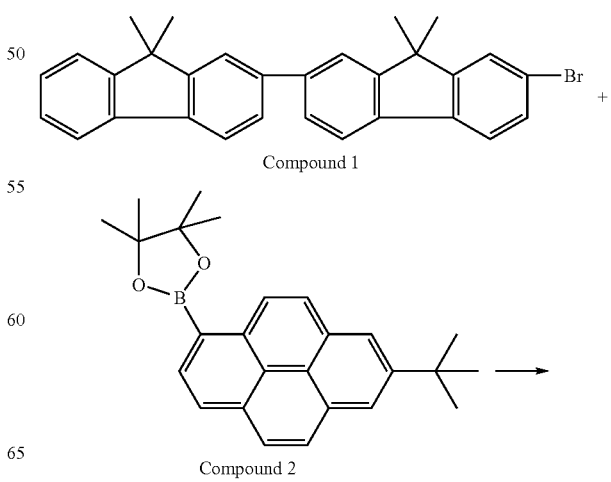

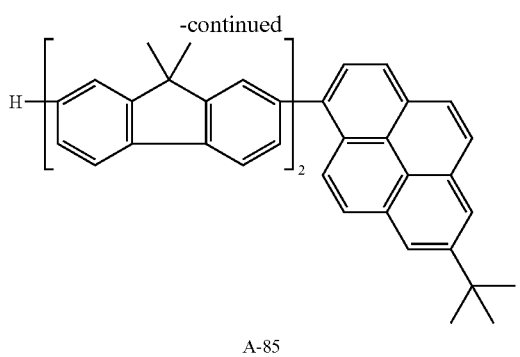

A-85

698 mg (1.5 mmole) of Compound 1 and 576 mg (1.5 mmole) of Compound 2 was prepared. These compounds and 15 ml of toluene, 7.5 ml of ethanol, 5 ml of a 2M aqueous solution of sodium carbonate, and 100 mg (0.09 mmole) of tetraxis(triphenylphosphine)paradium(0) were charged into a 100-ml flask, and the whole was stirred at 80° C. for 8 hours under nitrogen atmosphere. After the completion of the reaction, the reaction liquid was extracted with toluene, and then the organic layer was washed with water, dried with magnesium sulfate, and evaporated to dryness under reduced pressure. After being purified by silica gel column chromatography (eluent: toluene), recrystallization from toluene/ethanol was performed. The resultant crystal was vacuum-dried and then purified by sublimation to give 570 mg of Exemplified Compound No. A-85 (yield: 59.1%).

642.3 as M+ of the compound was confirmed by means of Matrix Assisted Laser Desorption/Ionization-Time of Flight Mass Spectrometry (MALDI-TOF MS).

The glass transition temperature of the compound in glassy state was measured with a differential scanning calorimeter (DSC) (Pyris 1 (trade name); manufactured by PerkinElmer) by increasing the temperature at a temperature rise rate of 20° C./min from room temperature and was thereby found to be 149° C. Further, when the compound was heated to its melting point, no recrystallization was observed, whereby it was confirmed that the compound was in a stable glassy state.

In addition, the structure of the compound was identified by NMR measurement.

$^1$H NMR (CDCl$_3$, 500 MHz) σ ppm): 8.27 (d, 1H, J=9.5 Hz), 8.23 (m, 3H), 8.01 (s, 2H), 8.04 (m, 2H), 7.94 (d, 1H, J=7.8 Hz), 7.90 (d, 1H, J=7.8 Hz), 7.83 (d, 1H, J=7.8 Hz), 7.79-7.65 (m, 7H), 7.48 (m, 1H), 7.36 (m, 2H), 1.67 (s, 6H), 1.60 (s, 9H), 1.59 (s, 6H)

Example 2

A transparent conductive support substrate was prepared which had a film of indium tin oxide (ITO) with a thickness of 120 nm as an anode formed on a glass substrate 1 by a sputtering method. The transparent conductive support substrate was ultrasonically cleaned sequentially with acetone and isopropyl alcohol (IPA), subsequently washed with boiled IPA, was then dried, was further cleaned with UV/ozone, and was used.

Then, on the transparent conductive support substrate, a chloroform solution of Compound 3 represented by the following structural formula was coated in a film thickness of 20 nm by spin coating method to form a hole-transporting layer.

Further, the following organic layers and electrode layers were successively formed by vacuum vapor deposition utilizing resistive heating in a vacuum chamber having an inner pressure of $10^{-5}$ Pa to thereby make a device.

Light-emitting layer (20 nm): Exemplified Compound No. A-85 and Compound 4 (10 wt. % concentration)
Electron-transporting layer (30 nm): Bphen (manufactured by DOJINDO LABORATORIES)
Metal electrode layer 1 (0.5 nm): LiF
Metal electrode layer 2 (150 nm): Al Compound 3

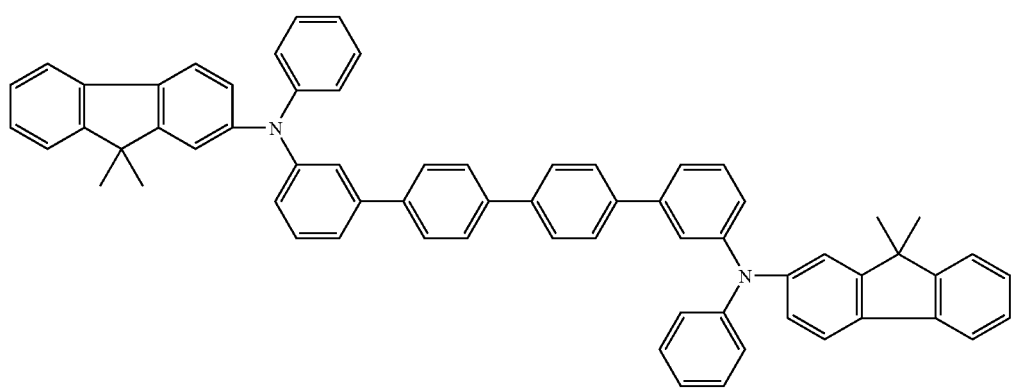

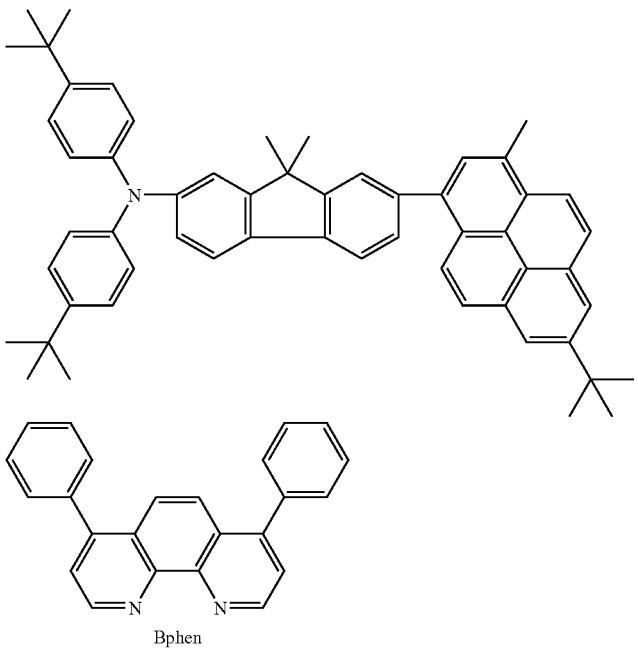

Bphen

The current-voltage characteristics of the EL device were measured by using a microammeter 4140B (manufactured by Hewlett-Packard Development Company), and the emission luminance thereof was measured by using a BM7 (manufactured by Topcon Corporation). When a voltage of 4.5 V was applied to the device of the present example, emission of a blue light was observed with an emission luminance of 1,739 cd/m² and an emission efficiency of 4.3 μm/W.

Furthermore, when a voltage was applied to the device in a nitrogen atmosphere for 100 hours so that the current density was kept at 33 mA/cm², the device emitted light at a luminance of about 2,100 cd/m² in an early stage and at about 1,500 cd/m² after the elapse of the 100 hours, which meant that the luminance degradation was small.

Example 3

Synthesis of Exemplified Compound No. A-91

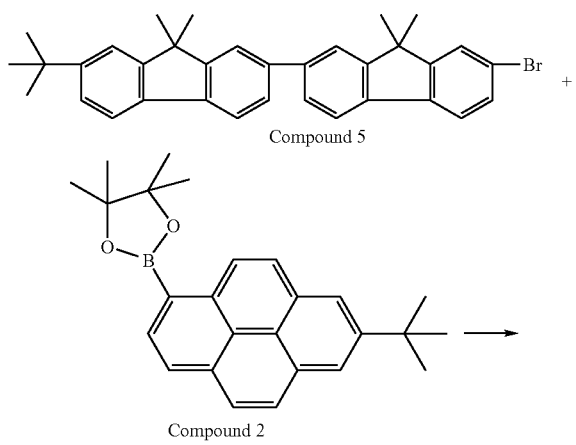

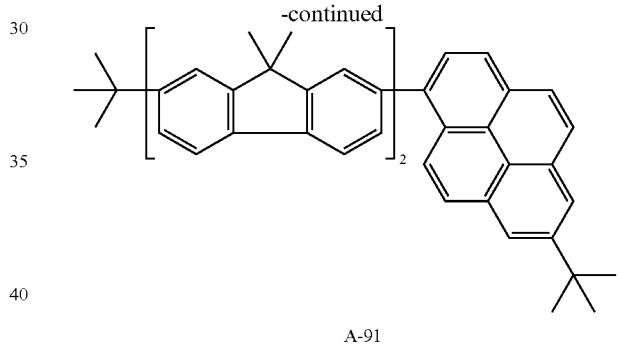

A-91

782 mg (1.5 mmole) of Compound 5 and 576 mg (1.5 mmole) of Compound 2 was prepared. These compounds and 15 ml of toluene, 7.5 ml of ethanol, 5 ml of a 2M aqueous solution of sodium carbonate, and 100 mg (0.09 mmole) of tetraxis(triphenylphosphine)paradium(0) were charged into a 100-ml flask, and the whole was stirred at 80° C. for 8 hours under nitrogen atmosphere. After the completion of the reaction, the reaction liquid was extracted with toluene, and then the organic layer was washed with water, dried with magnesium sulfate, and evaporated to dryness under reduced pressure. After being purified by silica gel column chromatography (eluent: toluene), recrystallization from toluene/ethanol was performed. The resultant crystal was vacuum-dried and then purified by sublimation to give 710 mg of Exemplified Compound No. A-91 (yield: 67.7%).

698.4 as M+ of the compound was confirmed by means of Matrix Assisted Laser Desorption/Ionization-Time of Flight Mass Spectrometry (MALDI-TOF MS).

The glass transition temperature of the compound was found to be 156° C. Further, when the compound was heated to its melting point, no recrystallization was observed, whereby it was confirmed that the compound was in a stable glassy state.

In addition, the structure of the compound was identified by NMR measurement.

$^1$H NMR (CDCl$_3$, 500 MHz) σ (ppm): 8.27 (d, 1H, J=9.1 Hz), 8.22 (m, 3H), 8.09 (s, 2H), 8.04 (m, 2H), 7.93 (d, 1H, J=7.6 Hz), 7.89 (d, 1H, J=7.9 Hz), 7.79 (d, 1H, J=7.9 Hz), 7.76 (m, 1H), 7.73-7.64 (m, 6H), 7.48 (m, 1H), 7.41 (m, 1H), 1.67 (s, 6H), 1.60 (s, 9H), 1.58 (s, 6H), 1.41 (s, 9H)

Example 4

A device was prepared by following the same procedure as in Example 2 with the exception that Exemplified Compound No. 91 was used in place of Exemplified Compound No. A-85 used in Example 2. When a voltage of 4.5 V was applied to the device of the present example, emission of a blue light was observed with an emission luminance of 601 cd/m$^2$ and an emission efficiency of 3.5 μm/W.

Furthermore, when a voltage was applied to the device in a nitrogen atmosphere for 100 hours so that the current density was kept at 33 mA/cm$^2$, the device emitted light at a luminance of about 1,800 cd/m$^2$ in an early stage and at about 1,000 cd/m$^2$ after the elapse of the 100 hours, which meant that the luminance degradation was small.

Example 5

Synthesis of Exemplified Compound No. B-1

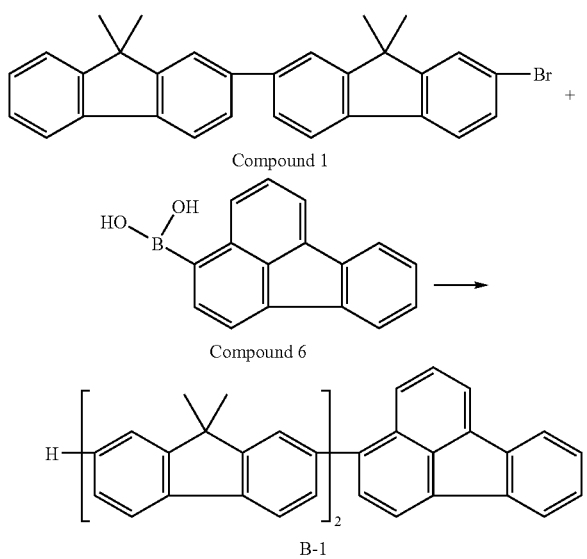

698 mg (1.5 mmole) of Compound 1 and 369 mg (1.5 mmole) of Compound 6 was prepared. These compounds and 15 ml of toluene, 7.5 ml of ethanol, 5 ml of a 2M aqueous solution of sodium carbonate, and 100 mg (0.09 mmole) of tetraxis(triphenylphosphine)paradium(0) were charged into a 100-ml flask, and the whole was stirred at 80° C. for 8 hours under nitrogen atmosphere. After the completion of the reaction, the crystal was filtered off and washed with water, ethanol, and toluene. The resulting crystal was recrystallized from chlorobenzene, then vacuum-dried at 120° C. and purified by sublimation to give 660 mg of Exemplified Compound No. B-1 (yield: 75.0%).

586.3 as M+ of the compound was confirmed by means of Matrix Assisted Laser Desorption/Ionization-Time of Flight Mass Spectrometry (MALDI-TOF MS).

The glass transition temperature of the compound was found to be 126° C. Further, when the compound was heated to its melting point, no recrystallization was observed, whereby it was confirmed that the compound was in a stable glassy state. In addition, the structure of the compound was identified by NMR measurement.

$^1$H NMR (CDCl$_3$, 500 MHz) σ (ppm): 8.02 (m, 4H), 7.99 (d, 1H, J=5.5 Hz), 7.96 (m, 2H), 7.91 (d, 1H, J=7.5 Hz), 7.88 (d, 1H, J=7.9 Hz), 7.82 (d, 1H, J=7.9 Hz), 7.77 (d, 1H, J=6.9 Hz), 7.74-7.62 (m, 8H), 7.47 (m, 1H), 7.41 (m, 1H), 7.36 (m, 1H), 1.66 (s, 6H), 1.59 (s, 6H)

Example 6

A device was prepared by following the same procedure as in Example 2 with the exception that Exemplified Compound No. B-1 was used in place of Exemplified Compound No. 4 used in Example 2. When a voltage of 4.5 V was applied to the device of the present example, emission of a blue light was observed with an emission luminance of 1,800 cd/m$^2$ and an emission efficiency of 5.01 lm/W.

Furthermore, when a voltage was applied to the device in a nitrogen atmosphere for 100 hours so that the current density was kept at 33 mA/cm$^2$, the device emitted light at a luminance of about 2,500 cd/m$^2$ in an early stage and at about 2,300 cd/m$^2$ after the elapse of the 100 hours, which meant that the luminance degradation was small.

Example 7

A transparent conductive support substrate was prepared which had a film of indium tin oxide (ITO) with a thickness of 120 nm as an anode formed on a glass substrate 1 by a sputtering method. The transparent conductive support substrate was ultrasonically cleaned sequentially with acetone and isopropyl alcohol (IPA), subsequently washed with boiled IPA, was then dried, was further cleaned with UV/ozone, and was used.

On the ITO substrate, the following organic layers and electrode layers were successively formed by vacuum vapor deposition utilizing resistive heating in a vacuum chamber having an inner pressure of 10$^{-5}$ Pa to thereby make a device.

Hole-transporting layer (20 nm): Compound 7

Light-emitting layer (20 nm): Exemplified Compound No. A-85 and Compound 4 (10 wt. % concentration)

Electron-transporting layer (30 nm): Bphen (manufactured by DOJINDO LABORATORIES)

Metal electrode layer 1 (0.5 nm): LiF

Metal electrode layer 2 (150 nm): Al

When a voltage of 4.5 V was applied to the device of the present example, emission of a blue light was observed with an emission luminance of 2,000 cd/m$^2$ and an emission efficiency of 3.0 μm/W.

Furthermore, when a voltage was applied to the device in a nitrogen atmosphere for 100 hours so that the current density was kept at 33 mA/cm$^2$, the device emitted light at a luminance of about 1,600 cd/m$^2$ in an early stage and at about 1,100 cd/m$^2$ after the elapse of the 100 hours, which meant that the luminance degradation was small.

Compound 7

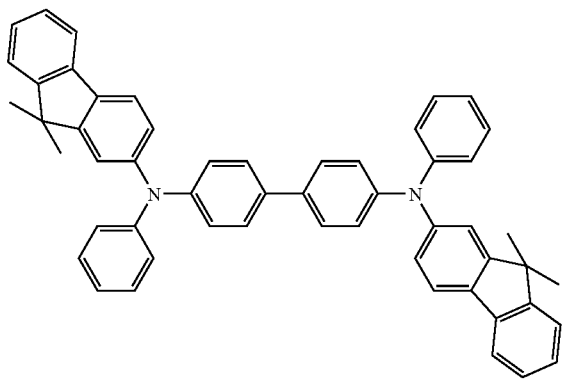

Example 8

Synthesis of Exemplified Compound No. A-1

Exemplified Compound No. A-1 can be synthesized by following the same procedure as in Example 1 with the exception that Compound 8 is used instead of Compound 2 used in Example 1.

Compound 8

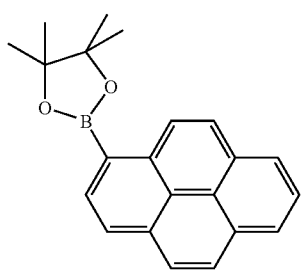

Example 9

Synthesis of Exemplified Compound No. A-1

Exemplified Compound No. A-2 can be synthesized by following the same procedure as in Example 1 with the exception that Compound 9 is used instead of Compound 1 used in Example 1 and that Compound 8 is used instead of Compound 2 used in Example 1.

Compound 9

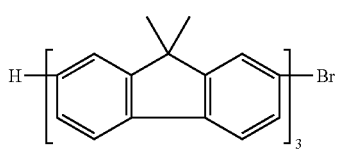

Example 10

Synthesis of Exemplified Compound No. A-3

Exemplified Compound No. A-3 can be synthesized by following the same procedure as in Example 1 with the exception that Compound 10 is used instead of Compound 1 used in Example 1 and that Compound 8 is used instead of Compound 2 used in Example 1.

Compound 10

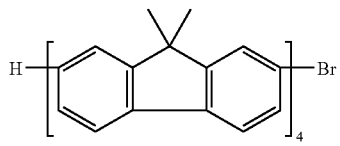

Example 11

Synthesis of Exemplified Compound No. A-19

Exemplified Compound No. A-19 can be synthesized by following the same procedure as in Example 3 with the exception that Compound 8 is used instead of Compound 2 used in Example 3.

Example 12

Synthesis of Exemplified Compound No. A-20

Exemplified Compound No. A-20 can be synthesized by following the same procedure as in Example 3 with the exception that Compound 11 is used instead of Compound 5 used in Example 3 and that Compound 8 is used instead of Compound 2 used in Example 3.

Compound 11

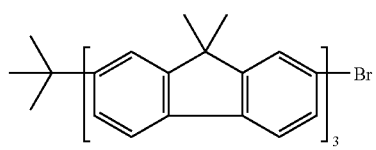

Example 13

Synthesis of Exemplified Compound No. A-28

Exemplified Compound No. A-28 can be synthesized by following the same procedure as in Example 1 with the exception that Compound 12 is used instead of Compound 1 used in Example 1 and that Compound 8 is used instead of Compound 2 used in Example 1.

Compound 12

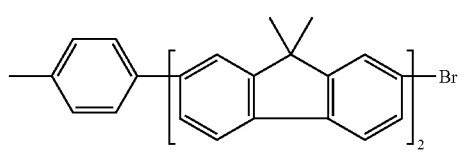

Example 14

Synthesis of Exemplified Compound No. A-40

Exemplified Compound No. A-40 can be synthesized by following the same procedure as in Example 1 with the exception that Compound 13 is used instead of Compound 1 used in Example 1 and that Compound 8 is used instead of Compound 2 used in Example 1.

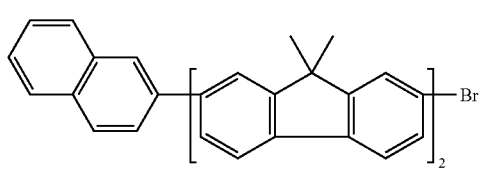

Compound 13

Example 15

Synthesis of Exemplified Compound No. A-73

Exemplified Compound No. A-73 can be synthesized by following the same procedure as in Example 1 with the exception that Compound 14 is used instead of Compound 1 used in Example 1 and that Compound 8 is used instead of Compound 2 used in Example 1.

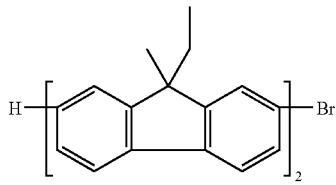

Compound 14

Example 16

Synthesis of Exemplified Compound No. A-86

Exemplified Compound No. A-86 can be synthesized by following the same procedure as in Example 1 with the exception that Compound 9 is used instead of Compound 1 used in Example 1.

Example 17

Synthesis of Exemplified Compound No. A-94

Exemplified Compound No. A-94 can be synthesized by following the same procedure as in Example 1 with the exception that Compound 15 is used instead of Compound 1 used in Example 1.

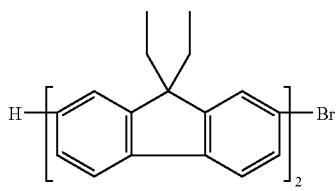

Compound 15

Example 18

Synthesis of Exemplified Compound No. A-103

Exemplified Compound No. A-103 can be synthesized by following the same procedure as in Example 1 with the exception that Compound 16 is used instead of Compound 2 used in Example 1.

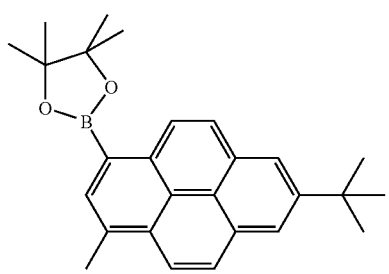

Compound 16

Example 19

Synthesis of Exemplified Compound No. A-104

Exemplified Compound No. A-104 can be synthesized by following the same procedure as in Example 1 with the exception that Compound 9 is used instead of Compound 1 used in Example 1 and that Compound 16 is used instead of Compound 2 used in Example 1.

Example 20

Synthesis of Exemplified Compound No. A-109

Exemplified Compound No. A-109 can be synthesized by following the same procedure as in Example 3 with the exception that Compound 16 is used instead of Compound 2 used in Example 3.

Example 21

Synthesis of Exemplified Compound No. A-122

Exemplified Compound No. A-122 can be synthesized by following the same procedure as in Example 1 with the exception that Compound 17 is used instead of Compound 2 used in Example 1.

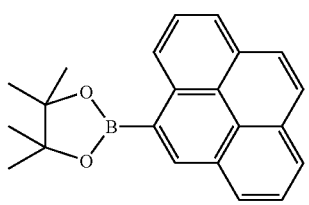

Compound 17

Example 22

Synthesis of Exemplified Compound No. A-49

Exemplified Compound No. A-49 can be synthesized by following the same procedure as in Example 1 with the exception that Compound 18 is used instead of Compound 1 used in Example 1 and that Compound 8 is used instead of Compound 2 used in Example 1.

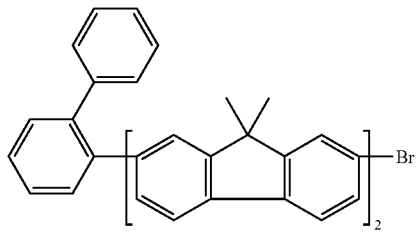

Compound 18

Example 23

Synthesis of Exemplified Compound No. A-52

Exemplified Compound No. A-52 can be synthesized by following the same procedure as in Example 1 with the exception that Compound 19 is used instead of Compound 1 used in Example 1 and that Compound 8 is used instead of Compound 2 used in Example 1.

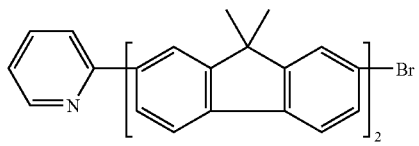

Compound 19

Example 24

Synthesis of Exemplified Compound No. A-64

Exemplified Compound No. A-64 can be synthesized by following the same procedure as in Example 1 with the exception that Compound 15 is used instead of Compound 1 used in Example 1 and that Compound 8 is used instead of Compound 2 used in Example 1.

Example 25

Synthesis of Exemplified Compound No. A-92

Exemplified Compound No. A-92 can be synthesized by following the same procedure as in Example 3 with the exception that Compound 11 is used instead of Compound 5 used in Example 3.

Example 26

Synthesis of Exemplified Compound No. A-93

Exemplified Compound No. A-93 can be synthesized by following the same procedure as in Example 1 with the exception that Compound 20 is used instead of Compound 1 used in Example 1.

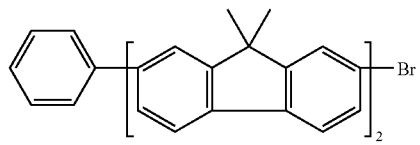

Compound 20

Example 27

Synthesis of Exemplified Compound No. A-99

Exemplified Compound No. A-99 can be synthesized by following the same procedure as in Example 1 with the exception that Compound 21 is used instead of Compound 1 used in Example 1.

Compound 21

Example 28

Synthesis of Exemplified Compound No. B-2

Exemplified Compound No. B-2 was synthesized by following the same procedure as in Example 5 with the exception that Compound 9 was used instead of Compound 1 used in Example 5 (yield: 70.7%).

778.4 as M+ of the compound was confirmed by means of Matrix Assisted Laser Desorption/Ionization-Time of Flight Mass Spectrometry (MALDI-TOF MS).

In addition, the structure of the compound was identified by NMR measurement.

$^1$H NMR (CDCl$_3$, 500 MHz) σ (ppm): 8.03 (m, 2H), 7.99 (d, 1H, J=6.8 Hz), 7.96 (m, 2H), 7.90 (m, 2H), 7.85 (m, 2H), 7.82 (d, 1H, J=7.8 Hz), 7.77 (m, 3H), 7.73-7.62 (m, 10H), 7.47 (m, 1H), 7.41 (m, 2H), 7.35 (m, 2H), 1.67 (s, 12H), 1.58 (s, 6H)

Example 29

Synthesis of Exemplified Compound No. B-19

Exemplified Compound No. B-19 can be synthesized by following the same procedure as in Example 5 with the exception that Compound 5 is used instead of Compound 1 used in Example 5.

Example 30

Synthesis of Exemplified Compound No. B-22

Exemplified Compound No. B-22 can be synthesized by following the same procedure as in Example 5 with the exception that Compound 20 is used instead of Compound 1 used in Example 5.

Example 31

Synthesis of Exemplified Compound No. B-25

Exemplified Compound No. B-25 can be synthesized by following the same procedure as in Example 5 with the exception that Compound 22 is used instead of Compound 1 used in Example 5.

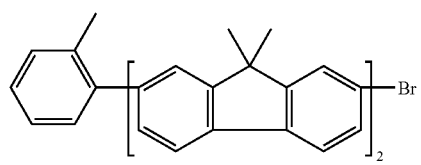

Compound 22

Example 32

Synthesis of Exemplified Compound No. B-31

Exemplified Compound No. B-31 can be synthesized by following the same procedure as in Example 5 with the exception that Compound 12 is used instead of Compound 1 used in Example 5.

Example 33

Synthesis of Exemplified Compound No. B-42

Exemplified Compound No. B-42 can be synthesized by following the same procedure as in Example 5 with the exception that Compound 15 is used instead of Compound 1 used in Example 5.

Example 34

Synthesis of Exemplified Compound No. B-60

Exemplified Compound No. B-60 can be synthesized by following the same procedure as in Example 5 with the exception that Compound 23 is used instead of Compound 6 used in Example 5.

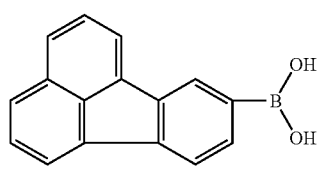

Compound 23

Example 35

A device was prepared by following the same procedure as in Example 7 with the exception that Exemplified Compound No. B-1 was used in place of Exemplified Compound No. A-85 used in Example 7 and that Coumarin 6 was used in 1 wt. % concentration in place of Compound 4 used in Example 7.

When a voltage of 4.0 V was applied to the device of the present example, emission of a green light was observed with an emission luminance of 3,000 cd/m$^2$.

Furthermore, when a voltage was continuously applied to the device in a nitrogen atmosphere, stable light emission was obtained during continuous voltage application for 100 hours.

Example 36

A device was prepared by following the same procedure as in Example 7 with the exception that Exemplified Compound No. B-1 was used in place of Exemplified Compound No. A-85 used in Example 7 and that Compound 24 was used in place of Compound 4 used in Example 7.

When a voltage of 4.5 V was applied to the device of the present example, emission of a blue light was observed with an emission luminance of 2,000 cd/m$^2$.

Furthermore, when a voltage was continuously applied to the device in a nitrogen atmosphere, stable light emission was obtained during continuous voltage application for 100 hours.

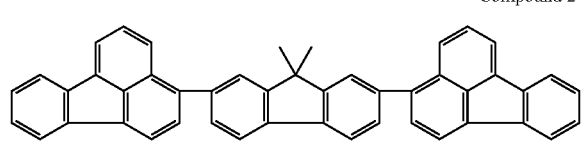

Compound 24

Example 37

Synthesis of Exemplified Compound No. A-133

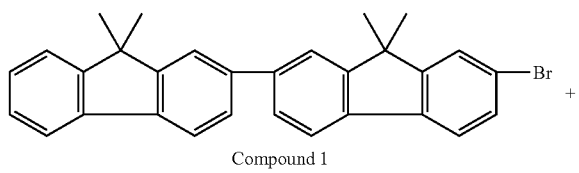

Compound 1

+

Compound 25

-continued

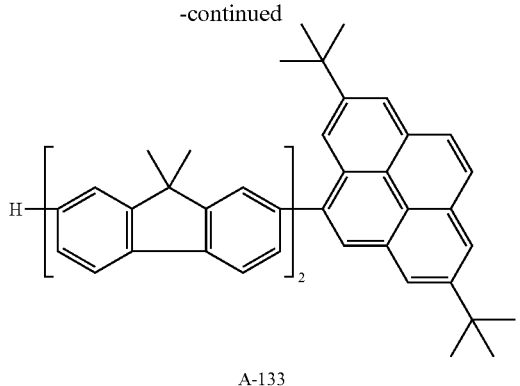

A-133

782 mg (1.5 mmole) of Compound 1 and 576 mg (1.5 mmole) of Compound 25 was prepared. These compounds and 15 ml of toluene, 7.5 ml of ethanol, 5 ml of a 2M aqueous solution of sodium carbonate, and 100 mg (0.09 mmole) of tetraxis(triphenylphosphine)paradium(0) were charged into a 100-ml flask, and the whole was stirred at 80° C. for 8 hours under nitrogen atmosphere. After the completion of the reaction, the reaction liquid was extracted with toluene, and then the organic layer was washed with water, dried with magnesium sulfate, and evaporated to dryness under reduced pressure. After being purified by silica gel column chromatography (eluent: toluene), recrystallization from toluene/ethanol was performed. The resultant crystal was vacuum-dried and then purified by sublimation to give 699 mg of Exemplified Compound No. A-133 (yield: 66.7%).

698.4 as M+ of the compound was confirmed by means of Matrix Assisted Laser Desorption/Ionization-Time of Flight Mass Spectrometry (MALDI-TOF MS).

In addition, the structure of the compound was identified by NMR measurement.

$^1$H NMR (CDCl$_3$, 500 MHz) σ (ppm): 8.37 (d, 1H), 8.23 (m, 2H), 8.20 (d, 2H), 8.07 (m, 3H), 7.96 (d, 1H), 7.91 (d, 1H), 7.81 (m, 2H), 7.77 (m, 2H), 7.73-7.68 (m, 4H), 7.48 (m, 1H), 7.36 (m, 2H), 1.67 (s, 6H), 1.59 (s, 15H), 1.48 (s, 9H)

Example 38

A device was prepared by following the same procedure as in Example 7 with the exception that Exemplified Compound No. A-133 was used in place of Exemplified Compound No. A-85 used in Example 7.

When a voltage of 4.5 V was applied to the device of the present example, emission of a blue light was observed with an emission luminance of 1,800 cd/m$^2$.

Furthermore, when a voltage was continuously applied to the device in a nitrogen atmosphere, stable light emission was obtained during continuous voltage application for 100 hours.

Example 39

Synthesis of Exemplified Compound No. C-2

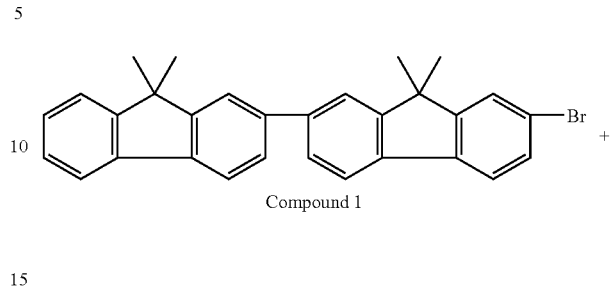

Compound 1

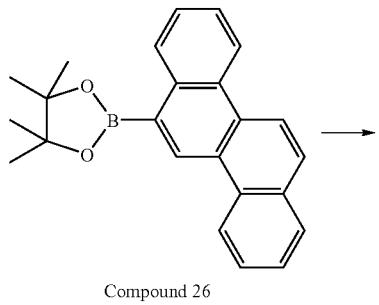

Compound 26

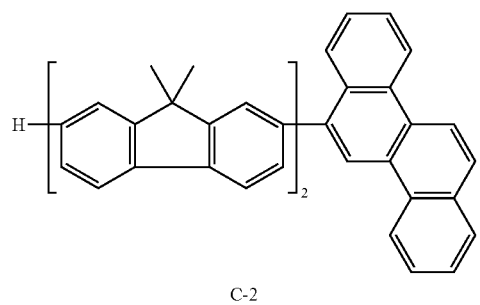

C-2

782 mg (1.5 mmole) of Compound 1 and 531 mg (1.5 mmole) of Compound 26 was prepared. These compounds and 15 ml of toluene, 7.5 ml of ethanol, 5 ml of a 2M aqueous solution of sodium carbonate, and 100 mg (0.09 mmole) of tetraxis(triphenylphosphine)paradium(0) were charged into a 100-ml flask, and the whole was stirred at 80° C. for 8 hours under nitrogen atmosphere. After the completion of the reaction, the reaction liquid was extracted with toluene, and then the organic layer was washed with water, dried with magnesium sulfate, and evaporated to dryness under reduced pressure. After being purified by silica gel column chromatography (eluent: toluene), recrystallization from toluene/ethanol was performed. The resultant crystal was vacuum-dried and then purified by sublimation to give 650 mg of Exemplified Compound No. C-2 (yield: 70.7%).

612.3 as M+ of the compound was confirmed by means of Matrix Assisted Laser Desorption/Ionization-Time of Flight Mass Spectrometry (MALDI-TOF MS).

In addition, the structure of the compound was identified by NMR measurement.

$^1$H NMR (CDCl$_{31}$, 500 MHz) σ (ppm): 8.90 (d, 1H), 8.79 (m, 3H), 8.13 (d, 1H), 8.02 (m, 2H), 7.93 (m, 2H), 7.83 (d, 1H), 7.74-7.61 (m, 11H), 7.47 (m, 1H), 7.35 (m, 2H), 1.67 (s, 6H), 1.59 (s, 6H)

Example 40

A device was prepared by following the same procedure as in Example 7 with the exception that Exemplified Compound No. C-2 was used in place of Exemplified Compound No. A-85 used in Example 7.

When a voltage of 4.5 V was applied to the device of the present example, emission of a blue light was observed with an emission luminance of 1,700 cd/m$^2$.

Furthermore, when a voltage was continuously applied to the device in a nitrogen atmosphere, stable light emission was obtained during continuous voltage application for 100 hours.

Example 41

A device was prepared by following the same procedure as in Example 6 with the exception that Exemplified Compound No. B-2 was used in place of Exemplified Compound No. B-1 used in Example 6.

When a voltage of 4.5 V was applied to the device of the present example, emission of a blue light was observed with an emission luminance of 1,800 cd/m$^2$.

Furthermore, when a voltage was continuously applied to the device in a nitrogen atmosphere, stable light emission was obtained during continuous voltage application for 100 hours.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions This application claims the benefit of Japanese Patent Application Nos. 2005-366559 filed Dec. 20, 2005, 2006-135070 filed May 15, 2006 and 2006-278926 filed Oct. 12, 2006 which are hereby incorporated by reference herein in their entirety.

The invention claimed is:

1. A compound represented by the following general formula (I):

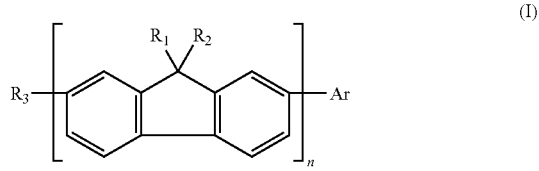

(I)

wherein $R_1$ and $R_2$ each represent, independently of one another, a substituted or unsubstituted alkyl group, a substituted or unsubstituted aralkyl group, a substituted or unsubstituted aryl group, or a substituted or unsubstituted heterocyclic group;

wherein $R_3$ represents a hydrogen atom, a linear, branched, or cyclic alkyl group (at least one methylene group of the alkyl group may be replaced by —O—, —S—, —CO—, —CO—O—, —O—CO—, —CH=CH—, —C≡C—, or a substituted or unsubstituted arylene group with one or two rings, and a hydrogen atom of the alkyl group may be replaced by a fluorine atom), a substituted or unsubstituted aryl group with one or two rings (at least one CH of the aryl group may be replaced by a nitrogen atom), where the aryl group may be substituted with an alkyl group, an aryl group, or a heterocyclic group;

wherein Ar represents a substituted or unsubstituted fused polycyclic aromatic group with four or more rings;

wherein n represents an integer of 2 to 10; and wherein the plurality of fluorene-2,7-diyl groups may each independently have a substituent and may be the same or different from each other.

2. The compound according to claim 1, wherein Ar of the general formula (I) is a fused polycyclic aromatic group represented by the following general formula (II):

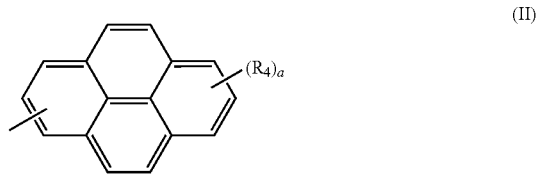

(II)

wherein $R_4$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, or a halogen atom;

wherein a represents an integer of 1 to 9; and wherein when $R_4$ is present in plurality, $R_4$ may be the same or different from each other.

3. The compound according to claim 1, which is represented by the following general formula (III):

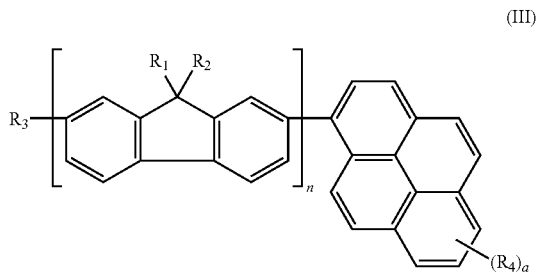

(III)

wherein $R_1$ and $R_2$ each represent, independently of one another, a substituted or unsubstituted alkyl group, a substituted or unsubstituted aralkyl group, a substituted or unsubstituted aryl group, or a substituted or unsubstituted heterocyclic group;

wherein $R_3$ represents a hydrogen atom, a linear, branched, or cyclic alkyl group (at least one methylene group of the alkyl group may be replaced by —O—, —S—, —CO—, —CO—O—, —O—CO—, —CH=CH—, —C≡C—, or a substituted or unsubstituted arylene group with one or two rings, and a hydrogen atom of the alkyl group may be replaced by a fluorine atom), a substituted or unsubstituted aryl group with one or two rings (at least one CH of the aryl group may be replaced by a nitrogen atom), where the aryl group may be substituted with an alkyl group, an aryl group, or a heterocyclic group;

wherein $R_4$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, or a halogen atom;

wherein a represents an integer of 1 to 9;

wherein when $R_4$ is present in plurality, $R_4$ may be the same or different from each other;

wherein n represents an integer of 2 to 10; and wherein the plurality of fluorene-2,7-diyl groups may each independently have a substituent and may be the same or different from each other.

4. The compound according to claim 1, wherein n of the general formula (I) is an integer of 2 to 4.

5. An organic light-emitting device comprising a pair of electrodes including an anode and a cathode, and a layer comprising an organic compound provided between the pair of electrodes, wherein the layer comprising the organic compound comprises at least one of the compounds set forth in claim 1.

6. The organic light-emitting device according to claim 5, wherein the layer is a light-emitting layer.

7. The organic light-emitting device according to claim 5, wherein the layer comprising the organic compound is a light-emitting layer which comprises at least two compounds of a host and a guest.

8. The organic light-emitting device according to claim 5, which is an electroluminescent device that emits light by application of a voltage to the pair of electrodes.

9. The organic light-emitting device according to claim 5, further comprising a color filter.

10. An apparatus comprising a substrate and the organic light-emitting device according to claim 5.

* * * * *